(12) United States Patent
Tsunoda et al.

(10) Patent No.: US 6,894,163 B2
(45) Date of Patent: May 17, 2005

(54) PROCESS FOR PREPARATION OF EPSILON-CAPROLACTAM

(75) Inventors: Takashi Tsunoda, Kurashiki (JP); Kenji Akagishi, Kurashiki (JP); Mitsuhiro Sekiguchi, Kurashiki (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 10/466,888

(22) PCT Filed: Feb. 14, 2002

(86) PCT No.: PCT/JP02/01270

§ 371 (c)(1),
(2), (4) Date: Jul. 22, 2003

(87) PCT Pub. No.: WO02/064560

PCT Pub. Date: Aug. 22, 2002

(65) Prior Publication Data

US 2004/0054169 A1 Mar. 18, 2004

(30) Foreign Application Priority Data

Feb. 14, 2001 (JP) .................................. 2001-037189
Mar. 8, 2001 (JP) .................................. 2001-065271

(51) Int. Cl.$^7$ ............................................. C07D 201/04
(52) U.S. Cl. .................................................... 540/536
(58) Field of Search ......................................... 540/536

(56) References Cited

U.S. PATENT DOCUMENTS

| | | |
|---|---|---|
| 4,709,024 A | 11/1987 | Sato et al. |
| 5,292,880 A | 3/1994 | Apelian et al. |
| 5,407,881 A | 4/1995 | Kitamura et al. |
| 5,741,904 A | 4/1998 | Hoelderich et al. |

FOREIGN PATENT DOCUMENTS

| | | |
|---|---|---|
| EP | 0 056 698 A2 | 7/1982 |
| EP | 0 236 092 A2 | 9/1987 |
| EP | 0 380 364 A2 | 8/1990 |
| EP | 0 388 070 A1 | 9/1990 |
| EP | 0 544 531 A1 | 6/1992 |
| EP | 0 544 530 A1 | 6/1993 |
| EP | 1 002 577 A1 | 5/2000 |
| JP | 6-107627 A | 4/1994 |
| JP | 7-324070 A | 12/1995 |
| JP | 10-87611 A | 4/1998 |

OTHER PUBLICATIONS

Herrero et al. (Latin American Applied Research (1994), 24(4), 195–202).*

* cited by examiner

*Primary Examiner*—Bruck Kifle
(74) *Attorney, Agent, or Firm*—Birch, Stewart, Kolasch & Birch, LLP

(57) ABSTRACT

ε-Caprolactam is produced by contacting cyclohexanone oxime with a solid acid catalyst in the gaseous phase to effect a rearrangement reaction of the cyclohexanone oxime. The solid acid catalyst is produced by calcining a dried catalyst precursor that can be a zeolite, a crystalline clay mineral and at least one substance selected from an inorganic oxide and a compound which forms the inorganic oxide by calcination. The inorganic oxide includes at least one element selected Groups 4, 13 and 14 of the Periodic Table, and the inorganic oxide excludes oxides contained in a crystalline form in the zeolite and the crystalline clay mineral. Alternately, the rearrangement reaction occurs in the presence of a polyhydric alcohol compound $R^1$—O—$R^2$—OH (where $R^1$ represents $C_1$–$C_5$ alkyl or phenyl, and $R^2$ represents $C_2$–$C_5$ alkylene).

18 Claims, 3 Drawing Sheets

Conversion of cyclohexanone oxime

Selectivity for ε-caprolactam

US 6,894,163 B2

PROCESS FOR PREPARATION OF EPSILON-CAPROLACTAM

This application is the national phase under 35 U.S.C. §371 of PCT International Application No. PCT/JP02/01270 which has an International filing date of Feb. 14, 2002, which designated the United States of America.

BACKGROUND OF THE INVENTION

1. Field of the Invention

The present invention relates to a method for producing ε-caprolactam from cyclohexanone oxime, the ε-caprolactam being useful as a raw material for producing nylon 6. More particularly, the present invention is concerned with a method for producing ε-caprolactam from cyclohexanone oxime, wherein the method includes the following first or second aspect: in the first aspect, the method comprises contacting cyclohexanone oxime with a specific solid acid catalyst in the gaseous phase to effect a rearrangement reaction of the cyclohexanone oxime, to thereby produce ε-caprolactam; or in the second aspect, the method comprises contacting cyclohexanone oxime with a solid acid catalyst in the gaseous phase to effect a rearrangement reaction of the cyclohexanone oxime, wherein the rearrangement reaction is effected in the presence of a specific polyhydric alcohol compound, to thereby produce ε-caprolactam.

The method of the present invention is advantageous not only in that ε-caprolactam can be produced with high selectivity and in high yield, but also in that the catalyst used in the method of the present invention can be shaped into a practical morphology useful in a commercial process, and also has excellent mechanical strength, so that the catalyst can be used for various catalytic reaction processes, such as those processes using a fixed-bed reactor, a fluidized-bed reactor and a moving-bed reactor; and the catalyst can also be used for a reaction process which is performed for a long time while frequently repeating a cycle of reaction and catalyst regeneration. Therefore, the method of the present invention is advantageous for producing ε-caprolactam stably for a long time.

2. Prior Art

ε-Caprolactam is known as an extremely important key chemical material for use in producing various chemical products, such as nylon 6. At present, commercial production of ε-caprolactam is mainly performed using a method which comprises contacting cyclohexanone oxime with an oleum catalyst (i.e., fuming sulfuric acid) in the liquid phase to effect a rearrangement reaction of the cyclohexanone oxime, to thereby produce ε-caprolactam. However, this method poses problems in that a large amount of ammonium sulfate is generated as a by-product, and that the reaction apparatus is corroded by the oleum. These problems have not yet been solved.

On the other hand, with respect to a method for producing ε-caprolactam, which comprises contacting cyclohexanone oxime with a solid acid catalyst in the gaseous phase, there have been a large number of proposals.

Unexamined Japanese Patent Application Laid-Open Specification No. Sho 57-139062 (corresponding to U.S. Pat. No. 4,359,421) discloses a method for producing ε-caprolactam by using a zeolite as the solid acid catalyst, wherein the zeolite has a silica/alumina ratio of 12 or more and a constraint index in the range of from 1 to 12, namely the zeolite is any of ZSM-5 zeolite and other specific ZSM zeolites.

Unexamined Japanese Patent Application Laid-Open Specification No. Sho 62-123167 (corresponding to U.S. Pat. No. 4,709,024) discloses a method for producing ε-caprolactam by using a crystalline zeolite catalyst which has a constraint index in the range of from 1 to 12, and which has an Si/Al atomic ratio of 500 or more and an external acid amount (the number of acidic sites observed on the crystal surface) of 5µ equivalent/g or less.

However, all of these methods have a common disadvantage caused by the sole use of the zeolite (which is the active species) as a catalyst.

In the commercial scale practice of a gaseous phase reaction process using a zeolite catalyst, it is very seldom to use a zeolite alone as a catalyst. Rather, in most cases, a zeolite is used in the form of a shaped article having an appropriate morphology, which is obtained by shaping a mixture of a zeolite with a conventional binder, such as a silica, a silica-alumina, or an alumina. This is because a zeolite is polycrystalline and, hence, is very difficult to shape into a desired morphology.

However, when a rearrangement reaction of cyclohexanone oxime for producing ε-caprolactam is performed using the above-mentioned zeolite in the form of a shaped article obtained by shaping a mixture of the zeolite with a conventional binder, such as a silica, a silica-alumina, or an alumina, there arises a problem in that, since those conventional binders are not inert to a reaction system for the above rearrangement reaction, the binders promote side reactions (e.g., reactions to by-produce a tar and a pitch), thus disadvantageously shortening the life of the catalyst and markedly reducing the catalytic activity and the selectivity for ε-caprolactam.

In an attempt to solve this problem, Unexamined Japanese Patent Application Laid-Open Specification No. 2000-202296 (corresponding to EP 1 002 577 A1) proposes a process for producing a catalyst which comprises an MFI zeolite and a siliceous ligand as main components, and which is suitable for use in a rearrangement reaction to convert an oxime into a corresponding amide. Specifically, the process proposed in this patent document comprises bonding the submicronic zeolite particles to a ligand obtained by acid hydrolysis (i.e., hydrolysis effected in an acidic solution) of a silicon alkoxide. However, this process has a disadvantage in that the catalyst production needs to be conducted while strictly controlling the production conditions, such as pH value and degree of dispersion of the zeolite, thus rendering complicated the production process.

Japanese Patent No. 3023581 (corresponding to U.S. Pat. No. 5,407,881) discloses a method using as a catalyst a zeolite shaped article having its strength improved by a treatment in which a pentasil type zeolite shaped article obtained without using any inorganic binder is contacted with an alkaline solution having a pH value in the range of from 9 to 13, at 30 to 100° C. However, when such a catalyst containing no inorganic binder as described above is used for a long time, the catalyst is likely to become powdery during the reaction due to the unsatisfactory mechanical strength of the catalyst. This method has also a disadvantage in that, when the catalyst containing no inorganic binder is subjected to further treatment for improving the strength of the catalyst, the production process becomes cumbersome.

Apart from the above-mentioned methods, there have also been disclosed methods for producing ε-caprolactam in the gaseous phase, in which the rearrangement reaction is effected in the copresence of a zeolite as a catalyst and a specific compound.

For example, EP 0 380 364 A2 discloses a method in which a gaseous phase reaction to produce ε-caprolactam from cyclohexanone oxime is effected in the copresence of a solid acid catalyst and a compound represented by the following formula: $R^1$—O—$R^2$ (wherein $R^1$ represents a lower alkyl group which may be substituted with a fluorine atom, and $R^2$ represents a hydrogen atom, a lower alkyl group or a phenyl group). That is, in this method, the reaction to produce ε-caprolactam is effected in the copresence of a solid acid catalyst and an ether compound or a lower alcohol.

Further, Unexamined Japanese Patent Application Laid-Open Specification No. Hei 10-87611 describes a method for producing ε-caprolactam, which comprises contacting cyclohexanone oxime with a catalyst selected from the group consisting of a ZSM-5 zeolite having an Si/Al atomic ratio of less than 100, a mordenite zeolite and a Y type zeolite, in the gaseous phase in the presence of an aliphatic alcohol having seven or more carbon atoms.

However, with respect to the above-mentioned patent documents which describe the use of a specific compound in combination with a zeolite, all of these patent documents use a zeolite alone as a catalyst and have no description about the use of a catalyst in the form of a practically useful shaped article obtained by shaping a zeolite using an appropriate binder.

Further, in practicing the production of ε-caprolactam by the rearrangement reaction of cyclohexanone oxime, in most cases, a carrier gas is used, for facilitating the contact between the raw material and the catalyst. In the actual process, it is necessary to separate the carrier gas used in the reaction from the above-described specific compound (such as an ether compound and/or a lower alcohol) used in combination with a zeolite.

However, when an ether compound and/or a lower alcohol are/is used, there arises a problem in that such compounds generally have a low boiling point, so that it is difficult to separate the carrier gas from the compounds.

On the other hand, when a higher alcohol is used, there arises a problem in that a higher alcohol generally has too high a boiling point which is close to the boiling point of cyclohexanone oxime, so that it is difficult to separate the cyclohexanone oxime from the higher alcohol.

SUMMARY OF THE INVENTION

In this situation, the present inventors have made extensive and intensive studies with a view toward developing a method for producing ε-caprolactam by contacting cyclohexanone oxime with a solid acid catalyst in the gaseous phase to effect a rearrangement reaction of the cyclohexanone oxime, which method is free from the above-mentioned problems accompanying the prior art, and can be used for stably and efficiently producing ε-caprolactam in high yield for a long time.

As a result, it has unexpectedly been found that this objective can be attained by a method comprising contacting cyclohexanone oxime with a solid acid catalyst in the gaseous phase to effect a rearrangement reaction of the cyclohexanone oxime, wherein the solid acid catalyst is produced by calcining a dried catalyst precursor, the catalyst precursor comprising a zeolite, a crystalline clay mineral and at least one substance selected from the group consisting of an inorganic oxide and a compound which forms the inorganic oxide by calcination, wherein the inorganic oxide comprises an oxide of at least one element selected from the group consisting of elements belonging to Groups 4, 13 and 14 of the Periodic Table (the "Periodic Table" mentioned herein is that prescribed in the IUPAC (International Union of Pure and Applied Chemistry) nomenclature system (1989)) and wherein the inorganic oxide is other than oxides contained in a crystalline form in the zeolite and the crystalline clay mineral. Based on this finding, the present invention has been completed.

The present inventors have also found that, by a specific method for producing ε-caprolactam, in which the above-mentioned rearrangement reaction is effected in the copresence of a solid acid catalyst and a specific polyhydric alcohol compound, the deactivation of the catalyst can be prevented and the selectivity for ε-caprolactam can be increased. The above-mentioned specific method comprises contacting cyclohexanone oxime with a solid acid catalyst in the gaseous phase to effect a rearrangement reaction of the cyclohexanone oxime, wherein the rearrangement reaction is effected in the presence of a polyhydric alcohol compound represented by the following formula: $R^1$—O—$R^2$—OH (wherein, $R^1$ represents a $C_1$–$C_5$ alkyl group or a phenyl group, and $R^2$ represents a $C_2$–$C_5$ alkylene group). Based on this novel finding, the present invention has been completed.

The foregoing and other objects, features and advantages of the present invention will be apparent from the following detailed description taken in connection with the accompanying drawings and the appended claims.

DETAILED DESCRIPTION OF THE INVENTION

Figure 1:
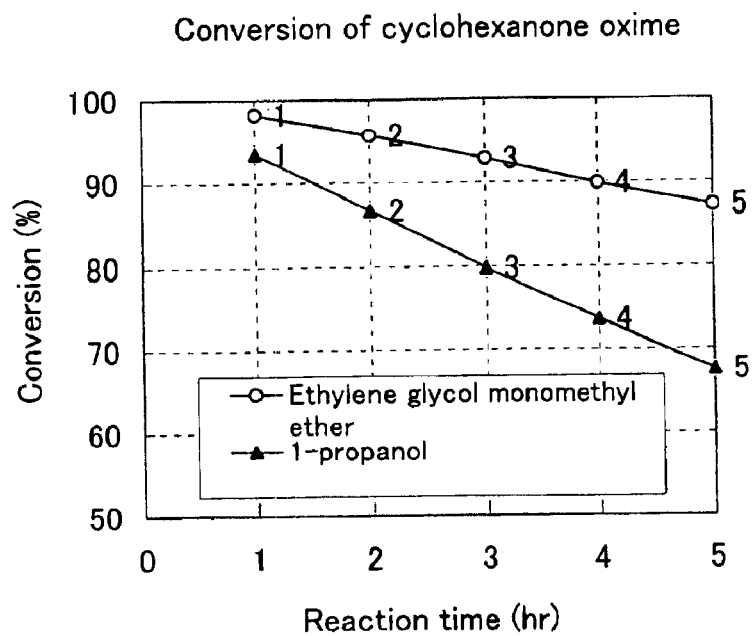
FIG. 1 is a graph showing a comparison in cyclohexanone oxime conversion between Example 16 and Comparative Example 5.

In a first aspect of the present invention, there is provided a method for producing ε-caprolactam, which comprises contacting cyclohexanone oxime with a solid acid catalyst in the gaseous phase to effect a rearrangement reaction of the cyclohexanone oxime, wherein the solid acid catalyst is produced by calcining a dried catalyst precursor, the catalyst precursor comprising a zeolite, a crystalline clay mineral and at least one substance selected from the group consisting of an inorganic oxide and a compound which forms the inorganic oxide by calcination, wherein the inorganic oxide comprises an oxide of at least one element selected from the group consisting of elements belonging to Groups 4, 13 and 14 of the Periodic Table and wherein the inorganic oxide is other than oxides contained in a crystalline form in the zeolite and the crystalline clay mineral.

In a second aspect of the present invention, there is provided a method for producing ε-caprolactam, which comprises contacting cyclohexanone oxime with a solid acid catalyst in the gaseous phase to effect a rearrangement reaction of the cyclohexanone oxime, wherein the rearrangement reaction is effected in the presence of a polyhydric alcohol compound represented by the following formula: $R^1$—O—$R^2$—OH (wherein: $R^1$ represents a $C_1$–$C_5$ alkyl group or a phenyl group, and $R_2$ represents a $C_2$–$C_5$ alkylene group).

For easy understanding of the present invention, the essential features and various preferred embodiments of the present invention are enumerated below.

1. A method for producing ε-caprolactam, which comprises contacting cyclohexanone oxime with a solid acid catalyst in the gaseous phase to effect a rearrangement reaction of the cyclohexanone oxime,
   the solid acid catalyst being produced by calcining a dried catalyst precursor, the catalyst precursor comprising a zeolite, a crystalline clay mineral and at least one substance selected from the group consisting of an inorganic oxide and a compound which forms the inorganic oxide by calcination, wherein the inorganic oxide comprises an oxide of at least one element selected from the group consisting of elements belonging to Groups 4, 13 and 14 of the Periodic Table and wherein the inorganic oxide is other than oxides contained in a crystalline form in the zeolite and the crystalline clay mineral.
2. The method according to item 1 above, wherein the zeolite is at least one member selected from the group consisting of an aluminosilicate having an Si/Al atomic ratio of 10 or more, a metallosilicate having an Si/metal atomic ratio of 10 or more and a silicalite.
3. The method according to item 1 or 2 above, wherein the zeolite is an MFI zeolite.
4. The method according to any one of items 1 to 3 above, wherein the zeolite is at least one member selected from the group consisting of an MFI silicalite and a ZSM-5 zeolite.
5. The method according to any one of items 1 to 4 above, wherein the crystalline clay mineral is at least one member selected from the group consisting of a kaolin mineral, a talc, a montmorillonite and a pyrophyllite.
6. The method according to any one of items 1 to 5 above, wherein the inorganic oxide is at least one member selected from the group consisting of a silica, a silica-alumina and an alumina.
7. The method according to any one of items 1 to 6 above, wherein the amount of the crystalline clay mineral in the dried catalyst precursor is from 5 to 50% by weight, based on the total weight of the zeolite, the crystalline clay mineral and the at least one substance selected from the group consisting of an inorganic oxide and a compound which forms the inorganic oxide by calcination.
8. The method according to any one of items 1 to 7 above, wherein the rearrangement reaction of the cyclohexanone oxime is performed under conditions wherein the reaction temperature is from 200 to 500° C., the reaction pressure is from 0.01 to 1 MPa, and the weight hourly space velocity of the cyclohexanone oxime is from 0.01 to 100 hr$^{-1}$.
9. The method according to any one of items 1 to 8 above, wherein the rearrangement reaction is performed by the fluidized-bed process.
10. The method according to any one of items 1 to 9 above, wherein a part of the catalyst used in the rearrangement reaction is continuously or intermittently withdrawn from a reactor for the rearrangement reaction, whereupon the withdrawn catalyst is regenerated in an atmosphere of oxygen-containing gas or an inert gas, and the regenerated catalyst is recycled to the reactor.
11. A method for producing ε-caprolactam, which comprises contacting cyclohexanone oxime with a solid acid catalyst in the gaseous phase to effect a rearrangement reaction of the cyclohexanone oxime, the rearrangement reaction being effected in the presence of a polyhydric alcohol compound represented by the following formula:

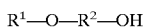

wherein:
   $R^1$ represents a $C_1$–$C_5$ alkyl group or a phenyl group, and
   $R^2$ represents a $C_2$–$C_5$ alkylene group.
12. The method according to item 11 above, wherein the solid acid catalyst is a zeolite or a zeolite-containing catalyst.
13. The method according to item 12 above, wherein the zeolite is at least one member selected from the group consisting of an aluminosilicate having an Si/Al atomic ratio of 10 or more, a metallosilicate having an Si/metal atomic ratio of 10 or more and a silicalite.
14. The method according to item 12 or 13 above, wherein the zeolite is an MFI zeolite.
15. The method according to any one of items 11 to 14 above, wherein the polyhydric alcohol compound is at least one member selected from the group consisting of ethylene glycol monomethyl ether, ethylene glycol monoethyl ether, propylene glycol monomethyl ether and propylene glycol monoethyl ether.
16. The method according to any one of items 11 to 14 above, wherein the polyhydric alcohol compound is ethylene glycol monomethyl ether.
17. The method according to any one of items 11 to 16 above, wherein the rearrangement reaction of the cyclohexanone oxime is performed under conditions wherein the reaction temperature is from 200 to 500° C., the reaction pressure is from 0.01 to 1 MPa, and the weight hourly space velocity of the cyclohexanone oxime is from 0.01 to 100 hr$^{-1}$.
18. The method according to any one of items 11 to 17 above, wherein the rearrangement reaction is performed by the fluidized-bed process.
19. The method according to any one of items 11 to 18 above, wherein a part of the catalyst used in the rearrangement reaction is continuously or intermittently withdrawn from a reactor for the rearrangement reaction, whereupon the withdrawn catalyst is regenerated in an atmosphere of oxygen-containing gas or an inert gas, and the regenerated catalyst is recycled to the reactor.

Hereinbelow, the present invention is described in detail.

In the method according to the first aspect of the present invention, it is required that a solid acid catalyst be used, wherein the solid acid catalyst is produced by calcining a dried catalyst precursor comprising a zeolite as a first component, a crystalline clay mineral as a second component, and, at least one substance as a third component, selected from the group consisting of an inorganic oxide and a compound which forms the inorganic oxide by calcination, wherein the inorganic oxide comprises an oxide of at least one element selected from the group consisting of elements belonging to Groups 4, 13 and 14 of the Periodic Table and wherein the inorganic oxide is other than oxides contained in a crystalline form in the zeolite and the crystalline clay mineral.

For improving the shapability and mechanical strength of the solid acid catalyst, in addition to the above-mentioned components, the dried catalyst precursor for the solid acid catalyst may further contain an additional component, such as a graphite, in an amount of from 1 to 5% by weight, based on the total weight of the first, second and third components of the dried catalyst precursor prior to the calcination.

The zeolite as a first component of the dried catalyst precursor is a porous crystalline silicate which is at least one member selected from the group consisting of an aluminosilicate, a metallosilicate and a silicalite, which are defined below. Further, the zeolite as defined in the present invention also encompasses a porous crystalline phosphate (such as SAPO-5 or SAPO-11) having substantially the same structure as that of a zeolite.

The aluminosilicate as defined in the present invention is a compound comprised mainly of $(SiO_4)^{4-}$ units and $(AlO_4)^{5-}$ units (hereinafter, both of the units are frequently referred to as "$TO_4$" which means a tetroxide of T atom having a tetrahedral structure with an oxygen atom positioned at each apex of the tetrahedral structure), wherein each $TO_4$ unit shares the four oxygen atoms at the apexes with the four neighboring $TO_4$ units, so that the $TO_4$ units are three-dimensionally bonded to form a crystal. The crystal is porous, and the diameters of openings of the pores of the crystal are in the range of from about 0.4 to about 0.8 nm. This crystal functions as a molecular sieve.

The metallosilicate as defined in the present invention has substantially the same porous crystal structure as that of the aluminosilicate, except that the crystal structure of the metallosilicate further comprises $TO_4$ units each having a metal atom other than Si and Al atoms as the T atom. Examples of such other metal atoms include titanium (Ti), boron (B), ferrum (Fe), zinc (Zn), gallium (Ga), chrome (Cr), cobalt (Co), zirconium (Zr), vanadium (V), copper (Cu), niobium (Nb) and beryllium (Be). Among these, boron (B) is not generally regarded as a metal; however, in the present invention, boron may be introduced to the crystal lattices of the metallosilicate as the T atom.

The silicalite as defined in the present invention has substantially the same porous crystal structure as that of the aluminosilicate, except that the crystal structure of the silicalite comprises substantially no $TO_4$ unit having Al atom or any of the above-mentioned other metal atoms as the T atom, but comprises only $TO_4$ units each having Si atom as the T atom.

The porous crystalline phosphate as defined in the present invention is comprised mainly of $(AlO_4)^{5-}$ units and $(PO_4)^{3-}$ units, which are the $TO_4$ units of the porous crystalline phosphate. In the porous crystalline phosphate, $(AlO_4)^{5-}$ units and $(PO_4)^{3-}$ units are bonded to one another to form a three-dimensional crystal structure. In general, the porous crystalline phosphates are collectively referred to as "$AlPO_4$-n" (wherein n is a positive integer and shows an identification number which is generally used for identifying the type of a porous crystalline phosphate, according to the crystal structure). Among the porous crystalline phosphates each containing $(AlO_4)^{5-}$ units and $(PO_4)^{3-}$ units, those which further contain $TO_4$ units having an Si atom as the T atom are referred to as "SAPO-n" (wherein n is a positive integer and shows an identification number which is generally used for identifying the type of a porous crystalline phosphate, according to the crystal structure), and those which further contain $TO_4$ units having any of Ga, Mg, Mn, Fe, Co, Zn and the like as the T atom are collectively referred to as "MeAPO". The porous crystalline phosphate has a similar structure to those of the zeolites as described above.

Among these, preferred are an aluminosilicate, a metallosilicate and a silicalite.

It is more preferred that the zeolite is at least one member selected from the group consisting of an aluminosilicate having an Si/Al atomic ratio of 10 or more, a metallosilicate having an Si/metal atomic ratio of 10 or more and a silicalite. It is still more preferred to use at least one member selected from the group consisting of an aluminosilicate having an Si/Al atomic ratio of 100 or more, a metallosilicate having an Si/metal atomic ratio of 100 or more and a silicalite. It is still more preferred to use an aluminosilicate having an Si/Al atomic ratio of 250 or more, a metallosilicate having an Si/metal atomic ratio of 250 or more and a silicalite. It is still more preferred to use at least one member selected from the group consisting of an aluminosilicate having an Si/Al atomic ratio of 500 or more, a metallosilicate having an Si/metal atomic ratio of 500 or more and a silicalite. It is most preferred to use an aluminosilicate having an Si/Al atomic ratio of 1000 or more, a metallosilicate having an Si/metal atomic ratio of 1000 or more and a silicalite.

Hereinbelow, specific examples of the above-mentioned zeolites are shown.

Examples of aluminosilicates include an A type zeolite, a X type zeolite, a Y type zeolite, an L type zeolite, an offretite zeolite, a mordenite zeolite, a ferrierite zeolite, and a ZSM-5 zeolite (see Examined Japanese Patent Application Publication No. Sho 46-10064 (corresponding to Canadian Patent No. 902,334)), a ZSM-11 zeolite (see Examined Japanese Patent Application Publication No. Sho 53-23280 (corresponding to U.S. Pat. No. 3,709,979)), a ZSM-12 zeolite (see Examined Japanese Patent Application Publication No. Sho 52-16079 (corresponding to U.S. Pat. No. 3,832,449)), a ZSM-23 zeolite ("ZEOLITES" 5, pp. 352–354, A. C. Rohrman Jr et al (1985)), a β type zeolite (see U.S. Pat. No. 3,308,069) and an MCM-22 zeolite (see U.S. Pat. No. 4,954,325).

Examples of metallosilicates include a titanosilicate (see U.S. Pat. No. 4,410,501), a borosilicate (see EP 7,081 B1 (corresponding to U.S. Pat. No. 4,456,582)).

Examples of silicalites include the silicalite as described in U.S. Pat. No. 4,061,724.

Examples of porous crystalline phosphates having a structure similar to that of a zeolite include SAPO-5 (see Unexamined Japanese Patent Application Laid-Open Specification No. Sho 59-35018 (corresponding to U.S. Pat. No. 4,440,871)), SAPO-11 (see Unexamined Japanese Patent Application Laid-Open Specification No. Sho 59-35018 (corresponding to U.S. Pat. No. 4,440,871)).

Each of the above patent documents describing various zeolites has a description on the X-ray diffraction pattern of the zeolite and on the process for producing the zeolite.

With respect to the A type zeolite, X type zeolite, Y type zeolite, L type zeolite, offretite zeolite, mordenite zeolite, ferrierite zeolite, ZSM-5 zeolite, and ZSM-11 zeolite, the compositions and structures thereof are described in "An Introduction to Zeolite Molecular Sieves", A. Dyer, pp. 12–37, U.K., 1988.

Among the above zeolites, it is preferred to use a silicalite, a ZSM-5 zeolite, a titanosilicate, a borosilicate, a β type zeolite, and a ferrierite zeolite, and it is more preferred to use a zeolite having an MFI type structure, such as an MFI type silicalite, a ZSM-5 zeolite or an MFI type titanosilicate.

The term "MFI" is an IUPAC code name used for defining the structure of a zeolite. Details on the structure corresponding to the code name are described in "Atlas of zeolite framework types", 5th edition, p. 13, Ch. Baerlocher, W. M. Meier and D. H. Olson (2001). The X-ray diffraction patterns of the MFI type zeolites are shown in an article entitled "Collection of simulated XRD powder patterns for zeolites", R. v. Ballmoos and J. B. Higgins ("ZEOLITES" vol. 10, No. 5, June 1990, pp. 442S–445S).

As the most preferred zeolites, there can be mentioned an MFI type aluminosilicate having an Si/Al atomic ratio of 1000 or more, an MFI type metallosilicate having an Si/metal atomic ratio of 1000 or more, and an MFI type silicalite.

These zeolites may be caused to carry hydrogen ions, various metal ions, various metal compounds and the like by conventional methods, such as an ion exchange method, an impregnation method and an adsorption method. Among these methods, preferred is an ion exchange method.

With respect to the type and amount of the metal which the zeolite is caused to carry, there is no particular limitation, and the type and amount of the metal can be appropriately chosen as long as no adverse effect is caused on the reaction performed in the method of the present invention. By the experiments performed by the present inventors, it has been found that, when the zeolite is caused to carry a metal atom belonging to Group 11 of the Periodic Table (i.e., Cu, Ag and Au) by the above-mentioned methods, such as an ion exchange, the life of the obtained catalyst can be prolonged. Among these metal atoms, Ag is most preferred.

Figure 5:
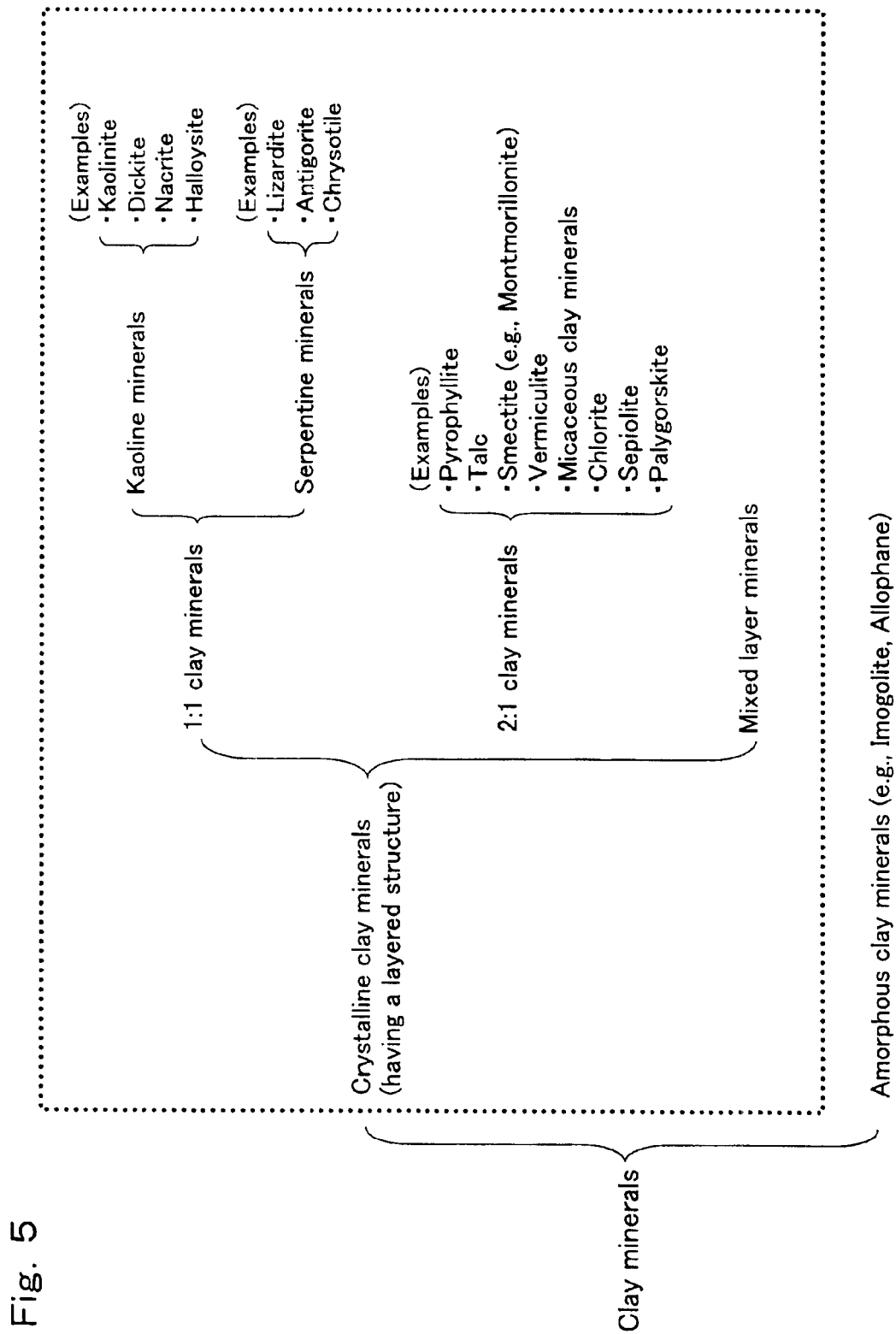
FIG. 5 is a chart showing the classification of crystalline clay minerals, wherein the crystalline clay minerals which can be contained in the catalyst precursor (before calcination) for the catalyst used in the first aspect of the present invention are shown within the dotted frame.

In the method according to the first aspect of the present invention, examples of crystalline clay minerals used as the second component include the crystalline clay minerals as shown within the dotted frame shown in FIG. 5.

Hereinbelow, an explanation is made on the clay minerals used in the present invention.

The following two basic units constitute clay minerals: an $SiO_4$ tetrahedron unit having a structure in which four $O^{2-}$ ions are coordination-bonded to an $Si^{4+}$ ion, and an $Al(OH)_6$ octahedron unit having a structure in which six $OH^-$ or $O^{2-}$ ions are coordination-bonded to an $Al^{3+}$ ion (provided that there is also an octahedron unit having a structure in which the $Al^{3+}$ ion in the $Al(OH)_6$ octahedron unit is replaced by an $Mg^{2+}$ or $Fe^{2+}$ ion). A sheet structure comprising a plurality of $SiO_4$ tetrahedron units which are two-dimensionally connected to each other is known as a "tetrahedral sheet", and a sheet structure comprising a plurality of $Al(OH)_6$ octahedron units which are two-dimensionally connected to each other is known as an "octahedral sheet".

In a clay mineral, layers of these tetrahedral sheet and octahedral sheet are laid upon each other.

Clay minerals are classified into three types in accordance with the layer structure comprising the sheets. That is, there are a "1:1 clay mineral", a "2:1 clay mineral", and a "mixed-layer mineral".

The 1:1 clay mineral is a clay mineral having a structure (1:1 structure) comprising a plurality of unit layers each comprised of one tetrahedral sheet having connected thereto one octahedral sheet. The 2:1 clay mineral is a clay mineral having a structure (2:1 structure) comprising a plurality of unit layers each comprised of one octahedral sheet having connected thereto two tetrahedral sheets. The mixed-layer mineral is a clay mineral comprising a combination of at least two different clay minerals having the structures as described above.

Specific examples of 1:1 clay minerals include a kaolin mineral having a theoretical chemical composition of $Al_2Si_2O_5(OH)_4$, and a serpentine mineral having a theoretical chemical composition of $Mg_3Si_2O_5(OH)_4$. Examples of kaolin minerals include kaolinite, dickite, nacrite, and halloysite containing intercalated water molecules. Examples of serpentine minerals include chrysotile, lizardite, and antigorite.

Specific examples of 2:1 clay minerals include pyrophyllite having a theoretical chemical composition of $Al_2Si_4O_{10}(OH)_2$, talc having a theoretical chemical composition of $Mg_3Si_4O_{10}(OH)_2$, a smectite represented by a montmorillonite, a vermiculite, a micaceous clay mineral, and a chlorite. Further examples of 2:1 clay minerals include sepiolite and palygorskite, each of which has a structure in which $SiO_4$ tetrahedron sheets are cyclically inverted to thereby form pores.

Specific examples of mixed-layer minerals include a mixed layer mineral comprising a combination of mica and smectite, and a mixed-layer mineral comprising a combination of kaolin mineral and montmorillonite.

Generally, some natural clay minerals contain an amorphous component, such as an amorphous silica, in addition to a crystalline clay mineral component.

The oxides (such as $SiO_2$ and $Al_2O_3$) contained in the crystalline clay mineral used as the second component of the solid acid catalyst used in the method according to the first aspect of the present invention, can form a crystalline structure, and thus the crystalline clay mineral has a structure in which such oxides are arranged regularly to thereby form a crystal. On the other hand, the inorganic oxide (comprising $SiO_2$, $Al_2O_3$ and the like) used as the third component (which is described below in detail) does not have a structure in which such oxides ($SiO_2$, $Al_2O_3$ and the like) are arranged regularly. Because of such a difference, the oxides contained in the second component and the inorganic oxide used as the third component can be distinguished from each other. That is, the inorganic oxide used as the third component is an inorganic oxide other than the crystalline oxides contained in a crystalline form in the zeolite and the crystalline clay mineral.

The clay mineral used in the present invention preferably has a crystalline clay mineral content of 50% by weight or more, more preferably 90% by weight or more. When an inorganic oxide other than the crystalline clay mineral is present in the clay mineral used, the inorganic oxide other than the crystalline clay mineral is regarded as a part of the inorganic oxide used as the third component and is considered accordingly in the calculation of the weight ratio of the second component of the solid acid catalyst.

The above-mentioned crystalline clay minerals are used individually or in combination. The crystalline clay minerals may be any of a natural clay mineral and a synthetic clay mineral.

Further, before used for producing the solid acid catalyst, the crystalline clay mineral may be subjected to a preliminary treatment, such as calcination, ion exchange or acid treatment.

Among these crystalline clay minerals, preferred are a kaolin mineral, pyrophyllite, talc and a montmorillonite. More preferred is a kaolin mineral, and still more preferred is kaolinite.

The crystalline clay mineral is added primarily for the purpose of improving the strength and thermal resistance of the catalyst shaped article. In addition, the use of the crystalline clay mineral as the second component of the solid acid catalyst in the rearrangement reaction of cyclohexanone oxime for producing ε-caprolactam in the method of the present invention (hereinafter, the rearrangement reaction is referred to simply as the "present reaction") is extremely effective for improving the selectivity for ε-caprolactam and prolonging the life of the catalyst, especially for improving the selectivity, as compared to the case of a catalyst containing no crystalline clay mineral (namely, a catalyst comprising only a zeolite and an inorganic oxide comprising an oxide of at least one element selected from the group consisting of elements belonging to Groups 4, 13 and 14 of the Periodic Table).

For the present reaction, the presence of aluminum is particularly disadvantageous because aluminum promotes the generation of by-products. Nevertheless, in the present invention, an advantageous effect can be obtained by the use of, for example, a kaolin mineral containing about 40% by weight of alumina. Indeed, such advantageous effect obtained by the use of a kaolin mineral is quite unexpected.

On the other hand, a catalyst shaped article comprising only a zeolite and a crystalline clay mineral does not exhibit satisfactory strength.

The third component of the dried catalyst precursor which is to be calcined to produce the solid acid catalyst used in the method according to the first aspect of the present invention, is at least one substance selected from the group consisting of an inorganic oxide and a compound which forms the inorganic oxide by calcination (hereinafter, the substance is frequently referred to as an "inorganic oxide and/or oxide-forming compound"). The third component of the dried catalyst precursor is added as a binder for the purpose of improving the strength of the catalyst shaped article. The inorganic oxide comprises an oxide of at least one element selected from the group consisting of elements belonging to Groups 4, 13 and 14 of the Periodic Table. The elements belonging to Group 4 of the Periodic Table are titanium (Ti), zirconium (Zr), and hafnium (Hf); the elements belonging to Group 13 of the Periodic Table are boron (B), aluminum (Al), gallium (Ga), indium (In), and thallium (Tl); and the elements belonging to Group 14 of the Periodic Table are carbon (C), silicone (Si), germanium (Ge), tin (Sn), and lead (Pb). Among these, preferred are oxides of Si, Al and Ti. More specifically, preferred are a silica, a silica-alumina, an alumina, a silica-titania, a titania, a silica-zirconia, and a zirconia; more preferred are a silica, a silica-alumina, and an alumina; and still more preferred is a silica. These oxides can be used individually or in combination. As described above, the inorganic oxide used as the third component is an inorganic oxide other than oxides contained in a regularly arranged crystalline form in the zeolite and the crystalline clay mineral.

Specific examples of compounds which form the inorganic oxide by calcination include hydroxides, such as $Al(OH)_3$, $Ti(OH)_4$, and $Zr(OH)_4$, and salts, such as $Al(NO_3)_3$ and the like.

With respect to the difference between the process for producing the catalyst used in the method according to the first aspect of the present invention and the above-mentioned process disclosed in Unexamined Japanese Patent Application Laid-Open Specification No. 2000-202296 (wherein a siliceous ligand which is obtained by subjecting a silicon alkoxide to an acid hydrolysis, is used as a binder for a zeolite), the difference resides in that the process of Unexamined Japanese Patent Application Laid-Open Specification No. 2000-202296 consists in performing an acid hydrolysis of a silicon alkoxide, whereas, in the production of the catalyst used in the method of the present invention, no problem occurs even when the inorganic oxide and the compound which forms the inorganic oxide by calcination are basic. Therefore, the process for producing the catalyst used in the present invention is advantageous in that the freedom of choice of raw materials is large and there can be used economical raw materials, and that no strict controlling of a pH value is required, rendering easy the production of the catalyst.

With respect to the ratio between a zeolite as the first component, a crystalline clay mineral as the second component, and an inorganic oxide and/or oxide-forming compound as the third component, it is preferred to use a zeolite as the first component in an amount of from 20 to 80% by weight, a crystalline clay mineral as the second component in an amount of from 5 to 50% by weight, and an inorganic oxide and/or oxide-forming compound as the third component in an amount of from 15 to 30% by weight, each based on the total weight of the first, second and third components of the dried catalyst precursor. It is more preferred to use a zeolite as the first component in an amount of from 30 to 70% by weight, a crystalline clay mineral as the second component in an amount of from 15 to 35% by weight, and an inorganic oxide and/or oxide-forming compound as the third component in an amount of from 15 to 35% by weight. When the amount of an inorganic oxide and/or oxide-forming compound as the third component is less than 15% by weight, the obtained catalyst shaped article tends to exhibit poor mechanical strength. When the amount of a crystalline clay mineral as the second component is less than 5% by weight, it is difficult for the obtained catalyst shaped article to exhibit the desired effect of improving selectivity.

Hereinbelow, an explanation is made on the process for producing the catalyst used in the method according to the first aspect of the present invention. With respect to the process for producing the catalyst, there is no particular limitation. However, it is generally preferred to use a process which comprises the following two steps: (1) a step of preparing a catalyst raw material mixture containing a zeolite as the first component, a crystalline clay mineral as the second component, and an inorganic oxide and/or oxide-forming compound as the third component; and (2) a step of subjecting the catalyst raw material mixture to molding, drying and calcination.

Hereinbelow, an explanation is made on the steps (1) and (2).

(1) Step of Preparing a Catalyst Raw Material Mixture

The catalyst raw material mixture comprises a zeolite as the first component, a crystalline clay mineral as the second component, and an inorganic oxide and/or oxide-forming compound as the third component.

As the zeolite, there can be used a zeolite obtained by hydrothermal synthesis performed using a conventional method as described, for example, in EP 0 380 364 A1. There can also be used a commercially available zeolite.

When the zeolite obtained by hydrothermal synthesis contains an organic template (i.e., an organic compound which is used to form a skeleton of the zeolite, such as tetrapropylammonium hydroxide), it is preferred that the organic template of the zeolite is decomposed by calcination before use, wherein the calcination for decomposition of the organic template is effected by subjecting the zeolite to a heat treatment in a furnace, such as an electric furnace or a tubular furnace, at a temperature in the range of from 400 to 700° C. for 1 to 24 hours, under an oxygen-containing atmosphere or a nitrogen-containing atmosphere.

If desired, a zeolite can be used in the form of an ion-exchanged zeolite, wherein the ion exchange is effected by a treatment of the zeolite with an aqueous solution of an inorganic salt, such as $NH_4NO_3$, $NH_4CL$ or $AgNO_3$. It is preferred that the ion exchange is effected by a method in which, to an aqueous inorganic salt solution is added a zeolite in an amount of from 1 to 30% by weight, based on the weight of the aqueous inorganic salt solution, and the resultant mixture is maintained at a temperature in the range of from 15 to 90° C. for 1 to 10 hours, followed by a filtration of the resultant reaction mixture, and the cycle of the ion exchange and filtration is then repeated 1 to 3 times. When an ammonium ion is converted into a hydrogen ion, it is preferred that the conversion of an ammonium ion into a hydrogen ion is effected by subjecting the zeolite to a heat treatment in a furnace, such as mentioned above, at a temperature in the range of from 400 to 600° C. for 1 to 10 hours under an atmosphere of air.

With respect to the crystalline clay mineral, a commercially available crystalline clay mineral as such can be used. Alternatively, before use, a commercially available crystalline clay mineral may be subjected to calcination at a temperature in the range of from 500 to 1,200° C.

With respect to the starting material for producing the inorganic oxide, it is preferred to use a sol, a gel or the like containing the component elements of the inorganic oxide. Examples of such starting materials include an aqueous sodium silicate solution, a silica sol, a silica gel (which is obtained by, for example, adding, to an aqueous sodium silicate solution, an acid, such as sulfuric acid, hydrochloric acid, or nitric acid), a silica-alumina sol, an alumina sol, a titania sol, and a zirconia sol. Preferred are an aqueous sodium silicate solution, a silica sol, a silica-alumina sol, and an alumina sol, and more preferred are an aqueous sodium silicate solution and a silica sol.

A silica sol, an alumina sol or the like used as the starting material for producing the inorganic oxide generally contains a trace amount of metal as an impurity, such as sodium. Therefore, the inorganic oxide contained in the dried catalyst precursor obtained by drying a raw material mixture containing such a starting material generally contains a trace amount of metal. With respect to the type and amount of the metal contained, there is no particular limitation. However, it is preferred that the amount of metal as an impurity is as small as possible, from the viewpoint of preventing the occurrence of an adverse effect on the present reaction.

The trace amount of metal can be removed from the dried catalyst precursor by subjecting the dried catalyst precursor to an acid treatment before calcination. With respect to the acid employed, there is no limitation; however, preferred are nitric acid, sulfuric acid, and hydrochloric acid.

It is preferred that the catalyst raw material mixture is provided in the form of a homogeneous dispersion containing these components for the dried catalyst precursor.

As a preferred example of a process for preparing the catalyst raw material mixture, there can be mentioned the following process. A predetermined amount of water is added to a raw material for the at least one substance selected from the group consisting of an inorganic oxide and a compound which forms the inorganic oxide by calcination, and the resultant aqueous mixture is stirred preferably by using a stirring device, such as a homogenizer or the like, at a revolution rate of from 2,000 to 10,000/minute for a time of from 15 minutes to 1 hour at room temperature. Then, to the mixture are added a zeolite and a crystalline clay mineral, preferably followed by stirring of the resultant mixture under substantially the same stirring conditions as mentioned above.

In the preparation of the catalyst raw material mixture, addition of water is not necessary. However, for improving the dispersibility of each component, it is preferred to add water in an amount which is from 0.5 to 20 times, more advantageously from 1 to 10 times, the total weight of the solids contained in the catalyst raw material mixture, namely, the total weight of the zeolite, the crystalline clay mineral, and the inorganic oxide (wherein, when a silica sol or the like, or a compound which forms the inorganic oxide by calcination is used, the amount thereof is expressed in terms of the amount of an inorganic oxide formed therefrom). Further, the preparation of a catalyst raw material mixture containing water may be performed by a process in which a zeolite and a crystalline clay mineral are dispersed into water, followed by stirring of the resultant aqueous mixture by using a homogenizer or the like under substantially the same conditions as mentioned above, to thereby obtain a slurry (zeolite/crystalline clay mineral aqueous mixture), and the obtained slurry is added to the remainder of the raw materials.

On the other hand, when an aqueous sodium silicate solution is used, it is preferred that a predetermined amount of an aqueous sodium silicate solution is preliminarily added to a 10 to 15% by weight aqueous sulfuric acid solution, thereby gelling $SiO_2$, and to the resultant mixture are added the above-mentioned zeolite/crystalline clay mineral aqueous mixture.

Anyway, it is important to homogeneously disperse a zeolite, a crystalline clay mineral and an inorganic oxide and/or a compound which forms the inorganic oxide by calcination, in the catalyst raw material mixture.

(2) Step of Subjecting the Catalyst Raw Material Mixture to Molding, Drying and Calcination The raw material mixture obtained in the above-mentioned step is subjected to molding, drying and calcination, to thereby obtain the catalyst used in the method of the present invention. Each operation is conducted in a manner which is appropriately selected in accordance with the mode of the rearrangement reaction in the method of the present invention. Representative examples of molding, drying and calcination are described hereinafter.

<Case of a Fluidized-bed Reaction>

In this case, the process for producing the catalyst comprises the steps of: spray drying the above-obtained raw material mixture (thereby obtaining a spherical catalyst precursor powder suitable for use in a fluidized-bed reactor) and calcining the obtained dried catalyst precursor.

In the spray drying step, spraying of the raw material mixture can be performed by centrifugation, by the two-phase flow nozzle method or by the high pressure nozzle method. As a heat source for drying, it is preferred to use air which has been heated by steam, an electric heater and the like. It is preferred that the temperature of the spray dryer at an entrance to the dryer section thereof is from 150 to 500° C. The thus heated air is caused to contact the raw material mixture in a counterflow or a parallel flow, causing the moisture in the raw material mixture to evaporate, to thereby obtain a dried catalyst precursor powder molded into a spherical shape having a diameter of about 20 to 150 μm. The obtained dried catalyst precursor powder is subjected to calcination in air by using a furnace, such as an electric furnace or a tubular furnace, at a temperature in the range of from 500 to 1,000° C. for 1 to 48 hours, preferably at a temperature in the range of from 600 to 800° C. for 1 to 10 hours.

<Case of a Fixed-bed Reaction>

In this case, the process for producing the catalyst comprises the steps of: drying or semi-drying the above-obtained raw material mixture; molding the obtained dried or semi-dried catalyst precursor into a cylindrical, a tubular or a granular form or the like, by employing a molding method, such as an extrusion molding method, a tableting method, or a compression molding method; and calcining the obtained shaped article of dried catalyst precursor.

In the case of an extrusion molding method, the catalyst raw material mixture is subjected to heat treatment, to thereby dehydrate the mixture to a level such that an extrusion molding can be appropriately effected (i.e., to dehydrate the mixture to a moisture content of about 10 to 40% by weight), and then the resultant semi-dried raw material mixture is subjected to an extrusion molding using an extrusion molding machine, to thereby obtain a solid cylindrically shaped article having a diameter of about 1 to 5 mm and a length of about 2 to 10 mm. The obtained shaped article is subjected to drying by using a dryer, at a temperature in the range of from 80 to 200° C., for 1 to 48 hours, to thereby obtain a dried catalyst precursor, and the dried catalyst precursor is then calcined under substantially the same conditions as mentioned above.

In the case of a tableting method or a compression molding method, the catalyst raw material mixture is sprayed onto an iron plate preheated to a temperature in the range of from 100 to 200° C., to thereby cause the moisture in the mixture to evaporate, and obtain a dried raw material mixture powder (a dry powder), followed by molding of the obtained dry powder either by tableting (i.e., a method in which the dry powder is pressed into a shaped article between the pounder and mortar of the tableting machine) or compressing, by the use of a tableting machine or a compression molding machine, to thereby obtain a shaped article of dried catalyst precursor. For improving the shapability of the dry powder (of a catalyst precursor), graphite or the like may be added to the dry powder, wherein the amount of graphite is from 1 to 5% by weight, preferably from 2 to 3% by weight, based on the weight of the dry powder. In a tableting method, it is preferred to mold the dry powder (of a catalyst precursor) into a cylindrical or a tubular form, each of which has a diameter of from 2 to 5 mm and a length of from 3 to 10 mm. In the case of a compression molding method, the shaped article of dried catalyst precursor may be worked by a method in which the shaped article is pulverized to form a particulate catalyst precursor, and the obtained particulate catalyst precursor is classified to thereby obtain particles having a desired particle size (e.g., in the range of from 0.3 to 3 mm). The thus obtained dried catalyst precursor is subjected to calcination under substantially the same conditions as mentioned above.

The method according to the first aspect of the present invention uses the thus obtained catalyst, i.e., a catalyst which is produced by calcining a dried catalyst precursor comprising a zeolite as a first component, a crystalline clay mineral as a second component and an inorganic oxide and/or oxide-forming compound as a third component. The method according to the first aspect of the present invention is advantageous not only in that the catalyst shaped article exhibits a satisfactory mechanical strength, but also in that a high selectivity for ε-caprolactam is achieved.

Hereinbelow, an explanation is made on the method according to the second aspect of the present invention.

In the method according to the second aspect of the present invention, preferred examples of solid acid catalysts include amorphous solid acid catalysts, such as silica-alumina, silica-magnesia and alumina-boria; non-crystalline solid acid catalysts having an orderly mesoporous structure, as represented by MCM-41 (see U.S. Pat. No. 5,098,684 and J. Am. Chem. Soc, 114, pp. 10834–10843, 1992); and crystalline solid acid catalysts, such as zeolites.

When a zeolite is used as the solid acid catalyst, there can be used the same zeolite as described above in connection with the method according to the first aspect of the present invention: namely, an aluminosilicate, a metallosilicate, and a silicalite. Among these, it is more preferred to use a silicalite, a ZSM-5 zeolite, a titanosilicate, a boron silicate, a β type zeolite and a ferrierite zeolite. Still more preferred are zeolites having an MFI type structure, such as an MFI type silicalite, a ZSM-5 zeolite, and an MFI type titanosilicate.

On the other hand, with respect to the Si/metal atomic ratio, it is more preferred to use at least one member selected from the group consisting of an aluminosilicate having an Si/Al atomic ratio of 10 or more, a metallosilicate having an Si/metal atomic ratio of 10 or more and a silicalite. It is still more preferred to use at least one member selected from the group consisting of an aluminosilicate having an Si/Al atomic ratio of 100 or more, a metallosilicate having an Si/metal atomic ratio of 100 or more and a silicalite. It is especially preferred to use at least one member selected from the group consisting of an aluminosilicate having an Si/Al atomic ratio of 250 or more, a metallosilicate having an Si/metal atomic ratio of 250 or more and a silicalite. It is still more preferred to use at least one member selected from the group consisting of an aluminosilicate having an Si/Al atomic ratio of 500 or more, a metallosilicate having an Si/metal atomic ratio of 500 or more and a silicalite. It is most preferred to use at least one member selected from the group consisting of an aluminosilicate having an Si/Al atomic ratio of 1000 or more, a metallosilicate having an Si/metal atomic ratio of 1000 or more and a silicalite.

Further, in the case of using a zeolite, the catalyst may be any of a catalyst composed only of a zeolite and a zeolite catalyst containing a conventional binder.

In the method according to the second aspect of the present invention, in the case where, for example, the solid acid catalyst comprises a zeolite and a binder, it is extremely advantageous to use the same second and third components as in the method according to the first aspect of the present invention, i.e., a crystalline clay mineral and at least one substance selected from the group consisting of an inorganic oxide (comprising an oxide of at least one element selected from the group consisting of elements belonging to Groups 4, 13 and 14 of the Periodic Table) and a compound which forms the inorganic oxide by calcination.

That is, the solid acid catalyst used in the method according to the first aspect of the present invention is preferred as the solid acid catalyst used in the method according to the second aspect of the present invention. In other words, it is preferred that the composition of the solid acid catalyst used in the method according to the second aspect of the present invention is the same as that of the solid acid catalyst used in the method according to the first aspect of the present invention.

In the method of the second aspect of the present invention, the polyhydric alcohol compound used in the rearrangement reaction is represented by the following formula:

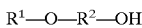

wherein:
R$^1$ represents a C$_1$–C$_5$ alkyl group or a phenyl group, and
R$^2$ represents a C$_2$–C$_5$ alkylene group.

Specific examples of such polyhydric alcohol compounds include ethylene glycol monomethyl ether, ethylene glycol monoethyl ether, ethylene glycol isopropyl ether, ethylene glycol monobutyl ether, ethylene glycol isobutyl ether, ethylene glycol isoamyl ether, ethylene glycol monophenyl ether, propylene glycol monomethyl ether, propylene glycol monoethyl ether, propylene glycol isopropyl ether, propylene glycol monobutyl ether, propylene glycol isobutyl ether, 1-methoxy-2-propanol, 1-methoxy-2-butanol, 3-methoxy-1-butanol, 3-methoxy-3-methyl butanol and the like.

It is more preferred to use at least one member selected from the group consisting of ethylene glycol monomethyl ether, ethylene glycol monoethyl ether, propylene glycol monomethyl ether and propylene glycol monoethyl ether. Still more preferred is ethylene glycol monomethyl ether. These can be used individually or in combination. Further, a part of the hydrogen atoms in $R^1$ may be replaced by a fluorine atom. These polyhydric alcohol compounds are solvents commonly used in the industry and are easily available.

By virtue of the presence of the polyhydric alcohol compound in the rearrangement reaction system, advantageous effects can be obtained in that a lowering of the catalyst activity is suppressed, and the selectivity for ε-caprolactam is greatly improved.

With respect to the manner of supplying the polyhydric alcohol compound into the reaction system, there is no particular limitation. The polyhydric alcohol compound may be supplied into the reaction system separately from cyclohexanone oxime. Alternatively, the supplying of the polyhydric alcohol compound may be performed by a method in which cyclohexanone oxime is dissolved into the polyhydric alcohol compound, and the resultant solution is supplied into the reaction system. Since the polyhydric alcohol compound is a good solvent for cyclohexanone oxime, it is preferred that the supplying of the polyhydric alcohol compound is performed by the above-mentioned alternative method (i.e., a method in which cyclohexanone oxime is dissolved into the polyhydric alcohol compound, and the resultant solution is supplied into the reaction system).

With respect to the amount of the polyhydric alcohol compound present in the reaction system, there is no particular limitation. However, it is preferred that the polyhydric alcohol compound is present in an amount which is 0.1 to 30 times the weight of the cyclohexanone oxime, more advantageously 0.5 to 20 times the weight of the cyclohexanone oxime, still more advantageously 1 to 10 times the weight of the cyclohexanone oxime.

If desired, other organic compounds may also be present in the reaction system. Examples of such other organic compounds include aromatic compounds, such as benzene and toluene, and aliphatic alcohols, such as methanol, ethanol, n-propanol, isopropanol, n-butanol, isobutanol, tert-butanol, n-amyl alcohol, n-hexanol, n-heptanol and n-octanol. Further examples of such other organic compounds include nitrile compounds, amide compounds, ether compounds and ketone compounds. When the other compounds are used, the amount of the other compounds is adjusted to a level which is not larger than the amount of the polyhydric alcohol compound.

Further, water, a basic substance (such as a methyl amine) and ε-caprolactam (which is the desired product) may also be supplied into the reaction system. By supplying these substances into the reaction system, the deterioration of the catalyst can be suppressed. When these substances are supplied into the reaction system, it is preferred that the amount of water is from 0.05 to 1.0 mole per mole of cyclohexanone oxime, and that the amount of each of an amine (such as methyl amine) and ε-caprolactam is from 0.05 to 0.5 mole per mole of cyclohexanone oxime.

In the method according to the first aspect of the present invention, cyclohexanone oxime alone may be supplied into the reaction system containing the catalyst. However, it is preferred that the reaction in the method according to the first aspect of the present invention is performed in the presence of the polyhydric alcohol compound used in the method according to the second aspect of the present invention. This is because, when the method according to the first aspect of the present invention is performed in such manner, the occurrence of side reactions by-producing a tar or a pitch can be suppressed, and the life of the catalyst can be remarkably prolonged, rendering it possible to produce ε-caprolactam stably in high yield for a long time.

Further, if desired, the "other organic compounds" as described above in connection with the method according to the second aspect of the present invention may be present in the reaction system in the method according to the first aspect of the present invention.

Hereinafter, explanations are made on the method of the present invention for producing ε-caprolactam by contacting cyclohexanone oxime with a solid acid catalyst in the gaseous phase, and the method for regenerating the catalyst used in the reaction. These explanations apply to both the methods according to the first and second aspects of the present invention.

The reaction is performed as follows. A solid acid catalyst is introduced into a reactor, such as a fixed-bed reactor, a moving-bed reactor or a fluidized-bed reactor. Cyclohexanone oxime (which is preliminarily evaporated in a vaporizer or is evaporated after it is supplied into the reactor) is contacted with the solid acid catalyst in the reactor in the gaseous phase under appropriate reaction conditions.

It is most preferred to perform the reaction by using the solid acid catalyst as described in connection with the first embodiment of the present invention, in the presence of the polyhydric alcohol compound as described in connection with the method according to the second aspect of the present invention.

Hereinbelow, an explanation is made on the reaction temperature and the reaction pressure. The term "reaction temperature" means a temperature at which a rearrangement reaction of cyclohexanone oxime in the present invention is performed to thereby produce ε-caprolactam. The term "reaction pressure" means a pressure under which the reaction is performed.

The reaction temperature is preferably from 200 to 500° C., more preferably from 300 to 450° C., still more preferably from 330 to 380° C. When the reaction temperature is lower than 200° C., the reaction rate tends to be unsatisfactory. When the reaction temperature is higher than 500° C., thermal decomposition of cyclohexanone oxime is likely to occur.

The reaction pressure is preferably from 0.01 to 1 MPa, more preferably from 0.03 to 0.5 MPa, still more preferably from 0.06 to 0.3 MPa.

The weight hourly space velocity (W.H.S.V.) of the cyclohexanone oxime as the starting material is preferably from 0.01 to 100 hour$^{-1}$, more preferably from 0.1 to 10 hour$^{-1}$.

The weight hourly space velocity (W.H.S.V.) is represented by the following formula:

$$W.H.S.V.=F/C \text{ (hour}^{-1}\text{)}$$

wherein:
F=amount of cyclohexanone oxime fed (kg/hour)
C=weight of catalyst (kg)

The reaction can be performed without using a carrier gas; however, it is preferred to use, for example, nitrogen gas, argon gas, carbon dioxide gas and hydrogen gas. With respect to the amount of carrier gas, there is no particular limitation. However, it is preferred that the carrier gas is present in an amount such that the cyclohexanone oxime concentration of the gaseous feedstock including the carrier gas is about 1 to 20% by volume.

When the catalyst has been deteriorated during the rearrangement reaction, the catalyst is subjected to an activation (regeneration) treatment for regeneration of the catalyst activity.

The regeneration treatment is performed by a method in which air itself or a gas obtained by diluting air with an inert gas (such as nitrogen gas, carbon dioxide gas or argon gas; preferably nitrogen gas) to a desired oxygen concentration (of about 1 to 10% by volume), or an inert gas, is flowed through a catalyst calcination apparatus maintained at a temperature and for a time which are sufficient to cause the tar, pitch or carbonaceous substances accumulated on the catalyst surface to burn, decompose and volatilize. In this case, it is preferred that the temperature is from 400 to 700° C. The time of maintaining the temperature for regeneration is generally from 0.5 to 48 hours.

The reaction used in the present invention (the present reaction) can be performed by various reactors for catalytic reaction processes, such as a fixed-bed reactor, a moving-bed reactor and a fluidized-bed reactor. Carbonaceous substances accumulate on the catalyst surface during the present reaction, thus gradually deactivating the catalyst. Therefore, it is preferred to perform the reaction by a reaction mode wherein the above-mentioned regeneration operation for activating a deteriorated catalyst can be periodically conducted. For example, in the case of a fixed-bed reaction process, it is preferred that the reaction is performed by using two or more reactors by a method in which the reaction and the catalyst regeneration are alternately performed in each reactor so as to perform the rearrangement reaction and the catalyst regeneration simultaneously in separate reactors.

On the other hand, in the case of a fluidized-bed reaction process, it is preferred that a part of the catalyst used in the rearrangement reaction is continuously or intermittently withdrawn from a reactor for the rearrangement reaction, whereupon the withdrawn catalyst is regenerated by using a regeneration apparatus in which the catalyst is heated at an appropriate temperature as described above, in an atmosphere of oxygen-containing gas or an inert gas, to thereby cause the carbonaceous substances accumulated on the catalyst surface to burn, decompose and volatilize, so that the carbonaceous substances are removed and the catalyst is regenerated. It is also preferred that the regenerated catalyst is continuously or intermittently recycled to the reactor. Especially, since the rearrangement reaction to convert cyclohexanone oxime into $\epsilon$-caprolactam is an exothermic reaction, it is most preferred to use a fluidized-bed reaction process, in which it is relatively easy to control the reaction temperature.

The isolation and purification of the obtained $\epsilon$-caprolactam from the gaseous reaction mixture can be performed by cooling/condensing the gaseous reaction mixture and recovering the resultant condensate, followed by an extraction, a distillation or a crystallization.

With respect to the polyhydric alcohol compound which was used in the present reaction, the polyhydric alcohol compound may be separated from the gaseous reaction mixture and reused.

BEST MODE FOR CARRYING OUT THE INVENTION

Hereinbelow, the present invention will be described in more detail with reference to the following Reference Examples, Examples and Comparative Examples, which should not be construed as limiting the scope of the present invention.

In the following Reference Examples, Examples and Comparative Examples, various measurements are conducted by the following methods.

(1) Measurement of Powder X-ray Diffraction Pattern of a Zeolite

A zeolite powder is analyzed by means of an apparatus described below, and the crystal structure of the zeolite is determined from the diffraction pattern obtained by the analysis.

The determination of the crystal structure of the zeolite is conducted, based on the information provided in an article entitled "Collection of simulated XRD powder patterns for zeolites", R. v. Ballmoos and J. B. Higgins ("ZEOLITES" vol. 10, No. 5, June 1990).

Apparatus: Powder X-ray Diffraction Measuring Apparatus (RAD-IIIA, manufactured and sold by Rigaku Corporation, Japan)

Measurement Conditions: CuK$\alpha$-ray

| X-ray tube voltage | 40 kV |
| X-ray tube current | 30 mA |
| Measurement angle 2$\theta$ | 5 to 45° |

(2) Measurements of the Si/Al Atomic Ratio and Si/Ti Atomic Ratio of a Zeolite

To 50 g of a 5 N aqueous NaOH solution is added 0.2 g of a zeolite. The resultant mixture is transferred to a Teflon microbomb, and the microbomb is hermetically sealed. The microbomb is heated in an oil bath maintained at a temperature of 150° C. for 12 to 70 hours to thereby completely dissolve the zeolite in the NaOH solution. The resultant solution having dissolved therein the zeolite is diluted with ion-exchanged water. (The degree of dilution suitable for the below-mentioned measurement by using an inductively coupled plasma emission spectrometer (hereinbelow, referred to as "ICP spectrometer") varies depending on the composition of the zeolite and the like. Therefore, the above-obtained solution having dissolved therein the zeolite is diluted approximately 5- to 100-fold so as to be suitable for the below-mentioned measurement by ICP.) The concentrations of silicon, aluminum and titanium are measured by ICP using the below-mentioned ICP spectrometer under the below-mentioned conditions, and the Si/Al atomic ratio and Si/Ti atomic ratio of the zeolite are calculated from the concentrations of silicon, aluminum and titanium.

ICP spectrometer and conditions for ICP spectrometry are as follows:

ICP spectrometer

JOBIN YVON (JY138 ULTRACE) (manufactured and sold by Rigaku Corporation, Japan)

Conditions for ICP

Wavelength for measuring the concentration of silicon: 251.60 nm

Wavelength for measuring the concentration of aluminum: 396.152 nm

Wavelength for measuring the concentration of titanium: 334.94 nm

Plasma power: 1.0 kW

Flow rate of the nebulizer gas: 0.28 liter/min

Flow rate of the sheath gas: 0.3 to 0.8 liter/min

Flow rate of the coolant gas: 13 liter/min (3) Analysis of a Reaction Product by Gas Chromatography A reaction mixture containing the produced $\epsilon$-caprolactam is analyzed by gas chromatography (GC) using the below-mentioned apparatus under the below-mentioned conditions, and the results of the reaction are evaluated (i.e., the cyclohexanone oxime conversion and selectivity for ε-caprolactam are calculated), based on the composition of the reaction mixture.

The GC apparatus and conditions for GC are as follows:

Apparatus: Gas chromatograph Model GC-17A, manufactured and sold by Shimadzu Corporation, Japan Column: Capillary column HR-20M (inner diameter: 0.25 mm, length: 50 m, and membrane thickness: 0.25 μm)

Pretreatment of sample: Before the gas chromatography analysis of the sample (reaction mixture), 3 g of a solvent used in the reaction for producing ε-caprolactam and 0.15 g of ethylbenzene as an internal standard are added to 1 g of the sample (the solvent and the sample are accurately weighed).

Amount of sample introduced into the column: 1 μl

Temperature elevation profile: The temperature of the sample is maintained at 100° C. for 5 minutes, elevated to 240° C. at a rate of 10° C./min, and then maintained at 240° C. for 42 minutes.

Split ratio: 100/1

Flow rate of carrier gas (nitrogen): 200 ml/min

Flame ionization detector (FID): Pressure of the supplied air=50 kPa (about 500 ml/min), pressure of the supplied hydrogen=60 kPa (about 50 ml/min)

(4) Measurement of Attrition Index of a Shaped Catalyst

The attrition index is generally used to evaluate the mechanical strength of powdery catalysts, such as those used in a fluidized-bed reaction. The attrition index is measured by subjecting a powdery catalyst to attrition test under specific conditions, and is defined as the degree of increase in the amount of particles having a size of 19 μm or less in the resultant catalyst. The smaller the attirtion index, the higher the attrition resistance.

Specific explanaions are made below with respect to the attrition test and the measurement of the attrition index.

25 g of a powdery catalyst is caused to contain 10% by weight of water, and the resultant catalyst is charged into a cylindrical attrition measuring apparatus (comprising a lower cylinder portion having a length of 27.5 inch and an inner diameter of 1.5 inch, an upper cylinder portion having a length of 22 inch and an inner diameter of 5 inch, and a vessel for collecting fine particles, which is provided on the top of the upper cylinder portion). Then, humidified air is blown into the apparatus through 3 pores (each having a diameter of 1/64 inch) formed at the bottom of the apparatus at a rate of 425 liter/hr, so as to circulate the catalyst in the apparatus for 5 hours to cause the attrition of the catalyst. Before and after the circulation of the catalyst in the attrition measuring apparatus, the catalyst is analyzed by means of an optical particle size distribution measuring apparatus, and the difference in the content of the fine particles (each having a size of 19 μm or less) between the catalyst before the circulation and the catalyst after the circulation.

The attrition index (I.D.) was calculated by the following formula:

$$I.D.=(A-B)/(C-B)\times 100$$

wherein:
  A: amount (g) of the fine particles (each having a size of 19 μm or less) in the catalyst after the 5 hour circulation,
  B: amount (g) of the fine particles (each having a size of 19 μm or less) in the catalyst before the 5 hour circulation, and
  C: amount (g) of the catalyst charged into the attrition measuring apparatus.

In the following Reference Examples 1 to 19, the catalysts used in Examples and Comparative Examples were prepared.

The compositions and characteristics of each of the crystalline clay minerals used in the following Reference Examples are mentioned below.

(1) Kaolinite

A hydrous kaolin "ASP072" (trade name; manufactured and sold by Engelhard Corporation, U.S.A.)

| | |
|---|---|
| Kaolinite content: | about 100% by weight |
| Composition: | $Al_2O_3$ 38.5% by weight |
| | $SiO_2$ 45.4% by weight |
| | $TiO_2$ 1.6% by weight |
| | Other trace metal components: 0.9% by weight |
| | Water of crystallization: 13.6% by weight |
| Average particle diameter: | 0.3 μm |

(2) Kaolinite

A calcined kaolinite "SATINTONE SP33" (trade name; manufactured and sold by Engelhard Corporation, U.S.A.)

| | |
|---|---|
| Kaolinite content: | about 100% by weight |
| Composition: | $Al_2O_3$ 44.3% by weight |
| | $SiO_2$ 52.2% by weight |
| | $TiO_2$ 1.8% by weight |
| | Other trace metal components: 1.2% by weight |
| | Water of crystallization: 0.5% by weight |
| Average particle diameter: | 1.4 μm |

(3) Pyrophyllite

"5M" (trade name; manufactured and sold by Tsuchiya Kaolin Co., Ltd., Japan)

| | |
|---|---|
| Pyrophyllite content: | about 60% by weight (the remainder is composed mainly of amorphous silica) |
| Composition: | $Al_2O_3$ 17.0% by weight |
| | $SiO_2$ 78.0% by weight |
| | Other trace metal components: 0.4% by weight |
| | Water of crystallization: 4.6% by weight |
| Average particle diameter: | 0.3 μm |

(4) Kaolinite

A hydrous kaolin "ASP600" (trade name; manufactured and sold by Engelhard Corporation, U.S.A.)

| | |
|---|---|
| Kaolinite content: | about 100% by weight |
| Composition: | $Al_2O_3$ 38.5% by weight |
| | $SiO_2$ 45.4% by weight |
| | $TiO_2$ 1.6% by weight |
| | Other trace metal components: 0.9% by weight |
| | Water of crystallization: 13.6% by weight |
| Average particle diameter: | 0.6 μm |

(5) Talc

"MICRO ACE K-1" (trade name; manufactured and sold by Nippon Talc Co., Ltd., Japan)

| | |
|---|---|
| Talc content: | about 100% by weight |
| Composition: | MgO 30.7% by weight |
| | SiO2 60.1% by weight |
| Other trace metal components: | 1.6% by weight |
| Water of crystallization: | 5.3% by weight |

REFERENCE EXAMPLE 1

Preparation of Catalyst (A)

To 130 g of tetraethyl orthosilicate was added 278 g of ethanol, and thereto was further added 291 g of a 10% by weight aqueous solution of tetrapropyl ammonium hydroxide. The resultant solution was stirred by using a homogenizer at a revolution rate of 5,000 rpm for 30 minutes, and then transferred to a 1-liter autoclave, followed by hydrothermal synthesis at 105 to 110° C. for 150 hours while stirring at a revolution rate of 500 rpm, to thereby obtain a slurry. The obtained slurry was subjected to filtration using a filter, and the resultant filtration residue was washed until it became almost neutral, and the washed filtration residue was dried at 120° C. for 12 hours, to thereby obtain a white crystal. The obtained crystal was calcined in air using an electric furnace at a temperature in the range of from 500 to 550° C. for 6 hours, and the resultant calcined product (zeolite) was subjected to a powder X-ray diffraction analysis as described above.

The X-ray diffraction analysis showed that the calcined product exhibited characteristic peaks at 10.99, 9.87, 3.83, 3.79, 3.73 and 3.69 in terms of the values (Å) of the interplanar spacings (d).

On the other hand, at page 444S of the article entitled "Collection of simulated XRD powder patterns for zeolites", written by R. v. Ballmoos and J. B. Higgins ("ZEOLITES", vol. 10, No. 5, June 1990), it is shown that, in a powder X-ray diffraction pattern of an MFI zeolite, an MFI zeolite exhibits characteristic peaks at 11.1±0.2, 10.0±0.2, 3.85±0.07, 3.80±0.05, 3.73±0.05 and 3.71±0.05 in terms of the (d) values, i.e., the interplanar spacings (d).

Since the above-mentioned results of the analysis of the obtained zeolite are well in agreement with these known (d) values of an MFI zeolite, the obtained zeolite was identified as an MFI zeolite.

The Si/Al atomic ratio of the obtained zeolite was measured according to the above-mentioned method. It was found that the zeolite had an Al content of 10 ppm or less, and an Si/Al atomic ratio of 45,000 or more (thus, it was determined that the zeolite contained substantially no Al). Therefore, the zeolite was identified as a silicalite.

The zeolite was added to a 7.5% by weight aqueous solution of ammonium nitrate, to thereby obtain a slurry having a solids content of 10% by weight, and the obtained slurry was subjected to an ion exchange at 80° C. for 2 hours. Thereafter, the slurry was subjected to filtration. Then, the cycle of the ion exchange and filtration was repeated twice, followed by washing with water, drying at 120° C. for 12 hours and calcination at 500° C. for 4 hours, to thereby obtain an H type silicalite. (The term "H type" used herein means that the zeolite was subjected to an ion exchange in an aqueous ammonium nitrate solution and then to calcination, to thereby cause the zeolite to carry hydrogen ions by ion exchange. Hereinafter, the term "H type silicalite" means a zeolite prepared by a synthesis process as described in this Reference Example 1.)

To 33.3 g of silica sol "SNOWTEX® STN30" (trade name; manufactured and sold by Nissan Chemical Industries Ltd., Japan; the silica sol has an $SiO_2$ content of 30% by weight, a sodium content of 700 ppm by weight and a pH value of 10, i.e., strongly basic) were added 137 g of purified water, 20 g of an H type silicalite, and 10 g of kaolinite "ASP072" (trade name), and the resultant mixture was stirred thoroughly to thereby obtain a slurry. The obtained slurry was sprayed, by using a small aerosol equipment, onto a hot plate preheated at 200° C., to thereby obtain a dried catalyst precursor powder. The thus obtained powder was calcined at 800° C. for 6 hours, to thereby obtain the catalyst (A). The above dried catalyst precursor powder had a composition wherein it comprised 50% by weight of an H type silicalite, 25% by weight of $SiO_2$, and 25% by weight of kaolinite.

For the sake of convenience, the composition of the dried catalyst precursor before calcination also is referred to as "composition of the catalyst (A)". This applies to all of the following Reference Examples 2 to 19.

REFERENCE EXAMPLE 2

Preparation of Catalyst (B) (Catalyst Containing no Crystalline Clay Minerals)

Catalyst (B) was prepared in substantially the same manner as in Reference Example 1, except that, to 66.7 g of silica sol "SNOWTEX® STN30" (trade name; manufactured and sold by Nissan Chemical Industries Ltd., Japan) were added 113 g of purified water and 20 g of an H type silicalite. The thus obtained catalyst (B) had a composition wherein it comprised 50% by weight of an H type silicalite and 50% by weight of $SiO_2$.

REFERENCE EXAMPLE 3

Preparation of Catalyst (C)

Catalyst (C) was prepared in substantially the same manner as in Reference Example 1, except that a silica sol (hereinafter, referred to as a "high purity silica sol") having a very small content of impurity metals was used (the high purity silica sol was prepared by the method described in the working examples of Unexamined Japanese Patent Application Laid-Open Specification No. Hei 4-231319 and had an $SiO_2$ content of 30% by weight, a sodium content of 120 ppm by weight or less and a pH value of 10 (that is, the silica sol was strongly basic). The thus obtained catalyst (C) had a composition wherein it comprised 50% by weight of an H type silicalite, 25% by weight of $SiO_2$, and 25% by weight of kaolinite.

REFERENCE EXAMPLE 4

Preparation of Catalyst (D) (Catalyst Containing no Crystalline Clay Minerals)

Catalyst (D) was prepared in substantially the same manner as in Reference Example 1, except that, to 66.7 g of the high purity silica sol were added 113 g of purified water and 20 g of an H type silicalite. The thus obtained catalyst (D) had a composition wherein it comprised 50% by weight of an H type silicalite and 50% by weight of $SiO_2$.

REFERENCE EXAMPLE 5

Preparation of Catalyst (E)

Catalyst (E) was prepared in substantially the same manner as in Reference Example 1, except that, to 25.0 g of the high purity silica sol were added 23.8 g of an alumina sol "Alumina sol 200" (trade name; manufactured and sold by Nissan Chemical Industries Ltd., Japan; the alumina sol had an $Al_2O_3$ content of 10.5% by weight and a pH value of from 4 to 6, that is, the alumina sol was weakly acidic), 121 g of purified water, 20 g of an H type silicalite and 10 g of kaolinite "ASP072" (trade name), and that the calcination temperature was 700° C. The thus obtained catalyst (E) had a composition wherein it comprised 50% by weight of an H type silicalite, 19% by weight of $SiO_2$, 6% by weight of $Al_2O_3$, and 25% by weight of kaolinite.

REFERENCE EXAMPLE 6

Preparation of Catalyst (F) (catalyst Containing no Crystalline Clay Minerals)

Catalyst (F) was prepared in substantially the same manner as in Reference Example 5, except that, to 50.0 g of the high purity silica sol were added 47.6 g of an alumina sol "Alumina sol 200" (trade name; manufactured and sold by Nissan Chemical Industries Ltd., Japan), 82 g of purified water and 20 g of an H type silicalite. The thus obtained catalyst (F) had a composition wherein it comprised 50% by weight of an H type silicalite, 38% by weight of $SiO_2$, and 12% by weight of $Al_2O_3$.

REFERENCE EXAMPLE 7

Preparation of Catalyst (G)

Catalyst (G) was prepared in substantially the same manner as in Reference Example 5, except that, to 95.2 g of an alumina sol "Alumina sol 200" (trade name; manufactured and sold by Nissan Chemical Industries Ltd., Japan) were added 275 g of purified water, 20 g of an H type silicalite and 10 g of kaolinite "ASP072" (trade name). The thus obtained catalyst (G) had a composition wherein it comprised 50% by weight of an H type silicalite, 25% by weight of $Al_2O_3$, and 25% by weight of kaolinite.

REFERENCE EXAMPLE 8

Preparation of Catalyst (H) (Catalyst Containing no Crystalline Clay Minerals)

Catalyst (H) was prepared in substantially the same manner as in Reference Example 5, except that, to 190 g of an alumina sol "Alumina sol 200" (trade name; manufactured and sold by Nissan Chemical Industries Ltd., Japan) were added 190 g of purified water and 20 g of an H type silicalite. The thus obtained catalyst (H) had a composition wherein it comprised 50% by weight of an H type silicalite and 50% by weight of $Al_2O_3$.

REFERENCE EXAMPLE 9

Preparation of Catalyst (I)

In Reference Example 9 was prepared catalyst (I) as defined in the present invention, which has a crystalline clay mineral content different from those in Reference Examples 1, 3, 5 and 7. Specifically, the preparation of the catalyst (I) was conducted as follows.

The catalyst (I) was prepared in substantially the same manner as in Reference Example 1, except that, to 53.3 g of the high purity silica sol were added 123 g of purified water, 20 g of an H type silicalite and 4 g of kaolinite "ASP072" (trade name). The thus obtained catalyst (I) had a composition wherein it comprised 50% by weight of an H type silicalite, 40% by weight of $SiO_2$ and 10% by weight of kaolinite.

REFERENCE EXAMPLE 10

Preparation of Catalyst (J)

Catalyst (J) was prepared in substantially the same manner as in Reference Example 1, except that, to 33.3 g of the high purity silica sol were added 137 g of purified water, 20 g of an H type silicalite and 10 g of talc "MICRO ACE K-1" (trade name; manufactured and sold by Nippon Talc Co., Ltd., Japan). The thus obtained catalyst (J) had a composition wherein it comprised 50% by weight of an H type silicalite, 25% by weight of $SiO_2$ and 25% by weight of talc.

REFERENCE EXAMPLE 11

Preparation of Catalyst (K)

Catalyst (K) was prepared in substantially the same manner as in Reference Example 1, except that, to 33.3 g of the high purity silica sol were added 137 g of purified water, 20 g of an H type silicalite and 10 g of montmorillonite "K-10" (trade name; manufactured and sold by Sigma-Aldrich Corporation, U.S.A.). The thus obtained catalyst (K) had a composition wherein it comprised 50% by weight of an H type silicalite, 25% by weight of $SiO_2$ and 25% by weight of montmorillonite.

REFERENCE EXAMPLE 12

Preparation of Catalyst (L)

10 g of kaolinite "ASP072" (trade name) and 18 g of an H type silicalite were added to an aqueous solution (strongly basic solution) containing 47.4 g of sodium silicate (grade: JIS Special-No. 3) (manufactured and sold by Fuji Chemical Co., Ltd., Japan; $SiO_2$ content=25.2% by weight, $Al_2O_3$ content=0.01% by weight, and $SiO_2/Na_2O$ molar ratio=3.3), 71 g of purified water and 6.0 g of a sulfuric acid. The resultant solution was stirred thoroughly by using a homogenizer at a revolution rate of 5,000 rpm, to thereby obtain a slurry. The obtained slurry was sprayed, by using a small aerosol equipment, onto a hot plate preheated at 200° C., to thereby obtain a dried catalyst precursor powder. The thus obtained dried catalyst precursor powder was added to 1 M aqueous solution of nitric acid to thereby obtain a slurry having a solids content of 10% by weight, and the obtained slurry was maintained at 25° C. for 1 hour, followed by washing with water, drying, and calcination at 600° C. for 5 hours, to thereby obtain the catalyst (L). The thus obtained catalyst (L) had a composition wherein it comprised 45% by weight of an H type silicalite, 30% by weight of $SiO_2$, and 25% by weight of kaolinite.

REFERENCE EXAMPLE 13

Preparation of Catalyst (M)

Catalyst (M) was prepared in substantially the same manner as in Reference Example 12, except that 10 g of kaolinite "SATINTONE SP33" (trade name) was used. The thus obtained catalyst (M) had a composition wherein it comprised 45% by weight of an H type silicalite, 30% by weight of $SiO_2$, and 25% by weight of kaolinite.

REFERENCE EXAMPLE 14

Preparation of Catalyst (N)

Catalyst (N) was prepared in substantially the same manner as in Reference Example 12, except that 10 g of pyrophyllite "5M" (trade name) was used. The thus obtained catalyst (N) had a composition wherein it comprised 45% by weight of an H type silicalite, 40% by weight of $SiO_2$, and 15% by weight of pyrophyllite.

REFERENCE EXAMPLE 15

Preparation of Catalyst (O)

Catalyst (O) was prepared in substantially the same manner as in Reference Example 12, except that 10 g of kaolinite "ASP600" (trade name) was used. The thus obtained catalyst (O) had a composition wherein it comprised 45% by weight of an H type silicalite, 30% by weight of $SiO_2$, and 25% by weight of kaolinite.

REFERENCE EXAMPLE 16

Preparation of Catalyst (P)

To 130 g of tetraethyl orthosilicate was added 78 g of ethanol, and thereto was further added an aqueous solution containing 65 g of purified water and 0.0886 g of titanium isopropoxide, and 291 g of a 10% by weight aqueous solution of tetrapropyl ammonium hydroxide. The resultant aqueous solution was subjected to a hydrothermal synthesis and an after-treatment in substantially the same manner as in Reference Example 1, to thereby obtain a white crystal. The obtained crystal was calcined in substantially the same manner as in Reference Example 1, and the resultant calcined product (zeolite) was subjected to a powder X-ray diffraction analysis as described above.

The X-ray diffraction analysis showed that the calcined product exhibited characteristic peaks at 10.99, 9.87, 3.83, 3.79, 3.73 and 3.69 in terms of the values (Å) of the interplanar spacings (d).

Since the above-mentioned results of the analysis of the obtained zeolite are well in agreement with these known (d) values of an MFI zeolite as described in the above-mentioned article, the obtained zeolite was identified as an MFI zeolite.

The Si/Ti atomic ratio of the obtained zeolite was measured according to the above-mentioned method. It was found that the zeolite had an Si/Ti atomic ratio of 1900. Therefore, the zeolite was identified as a titanosilicate. Further, the zeolite was subjected to an ion exchange in substantially the same manner as in Reference Example 1, to thereby obtain an H type titanosilicate.

Then, catalyst (P) was prepared in substantially the same manner as in Reference Example 3 except that, instead of the H type silicalite, the above-obtained H type titanosilicate was mixed with kaolinite "ASP072" (trade name) and a high purity silica sol. The thus obtained catalyst (P) had a composition wherein it comprised 50% by weight of an H type titanosilicate, 25% by weight of $SiO_2$ and 25% by weight of kaolinite.

REFERENCE EXAMPLE 17

Preparation of Catalyst (Q)

To 130 g of tetraethyl orthosilicate was added 278 g of ethanol, and thereto was further added an aqueous solution obtained by dissolving 0.197 g of 14–18 hydrate of aluminum sulfate in 13 g of purified water, and 291 g of a 10% by weight aqueous solution of tetrapropyl ammonium hydroxide. The resultant aqueous solution was subjected to a hydrothermal synthesis and an after-treatment in substantially the same manner as in Reference Example 1, to thereby obtain a white crystal. The obtained crystal was calcined in substantially the same manner as in Reference Example 1, and the resultant calcined product (zeolite) was subjected to a powder X-ray diffraction analysis as described above.

The X-ray diffraction analysis showed that the calcined product exhibited characteristic peaks at 10.99, 9.87, 3.83, 3.79, 3.73 and 3.69 in terms of the values (Å) of the interplanar spacings (d).

Since the above-mentioned results of the analysis of the obtained zeolite are well in agreement with these known (d) values of an MFI zeolite as described in the above-mentioned article, the obtained zeolite was identified as an MFI zeolite.

The Si/Al atomic ratio of the obtained zeolite was measured according to the above-mentioned method. It was found that the zeolite had an Si/Al atomic ratio of 1000. Therefore, the zeolite was identified as a ZSM-5 zeolite. Further, the zeolite was subjected to an ion exchange in substantially the same manner as in Reference Example 1, to thereby obtain an H type ZSM-5 zeolite (having an Si/Al atomic ratio of 1000).

Then, catalyst (Q) was prepared in substantially the same manner as in Reference Example 3 except that, instead of the H type silicalite, the above-obtained H type ZSM-5 zeolite (having an Si/Al atomic ratio of 1000) was mixed with kaolinite "ASP072" (trade name) and a high purity silica sol, and that the calcination temperature was 600° C. The thus obtained catalyst (Q) had a composition wherein it comprised 50% by weight of an H type ZSM-5 zeolite (having an Si/Al atomic ratio of 1000), 25% by weight of $SiO_2$ and 25% by weight of kaolinite.

REFERENCE EXAMPLE 18

Preparation of Catalyst (R)

A β type zeolite "CP814B-50" (trade name; manufactured and sold by Zeolyst International, U.S.A.; the zeolite has an Si/Al atomic ratio of 25) was subjected to a powder X-ray diffraction analysis. The analysis showed that the zeolite exhibited characteristic peaks at 11.58, 6.56, 4.16, 3.94 and 3.01 in terms of the values (Å) of the interplanar spacings (d).

On the other hand, in U.S. Pat. No. 3,308,069, it is shown that, in a powder X-ray diffraction pattern of a β type zeolite, a β type zeolite exhibits characteristic peaks at 11.4±0.2, 6.7±0.2, 4.25±0.1, 3.97±0.1 and 3.0±0.1 in terms of the (d) values, i.e., the interplanar spacings (d).

Since the above-mentioned known (d) values of a β type zeolite are well in agreement with the results of the analysis of the zeolite used herein, the zeolite used herein was identified as a β type zeolite.

The zeolite was added to a 1 M aqueous solution of ammonium chloride to thereby obtain a slurry having a solids content of 10% by weight, and the resultant slurry was subjected to an ion exchange at 70° C. for 3 hours, followed by filtration and washing with water, drying at 120° C. for 12 hours, and calcination at 500° C. for 4 hours, to thereby obtain an H-β type zeolite.

Then, catalyst (R) was prepared in substantially the same manner as in Reference Example 17, except that, instead of the H type ZSM-5 zeolite (having an Si/Al atomic ratio of 1000), mixed with kaolinite "ASP072" (trade name) and the high purity silica sol. The thus obtained catalyst (R) had a composition wherein it comprised 50% by weight of an H-β type zeolite, 25% by weight of $SiO_2$ and 25% by weight of kaolinite.

REFERENCE EXAMPLE 19

Preparation of Catalyst (S)

A ferrierite (zeolite) "CP914" (trade name: manufactured and sold by Zeolyst International, U.S.A.; Si/Al atomic ratio=28) was subjected to a powder X-ray diffraction analysis. The analysis showed that the zeolite exhibited characteristic peaks at 9.38, 5.62, 3.97, 3.53 and 3.45 in terms of the values (Å) of the interplanar spacings (d).

On the other hand, at page 398S of the article entitled "Collection of simulated XRD powder patterns for zeolites", R. v. Ballmoos and J. B. Higgins ("ZEOLITES", vol. 10, No. 5, June 1990), it is shown that, in a powder X-ray diffraction pattern of a ferrierite, a ferrierite exhibits characteristic peaks at 9.58±0.2, 5.82±0.2, 4.00±0.1, 3.53±0.05 and 3.49±0.05 in terms of the (d) values, i.e., the interplanar spacings (d).

Since the above-mentioned known (d) values of a ferrierite are well in agreement with the results of the analysis of the zeolite used herein, the zeolite used herein was identified as a ferrierite.

The ferrierite was subjected to an ion exchange in substantially the same manner as in Reference Example 18, to thereby obtain an H type ferrierite.

Then, catalyst (S) was prepared in substantially the same manner as in Reference Example 17, except that, instead of the H type ZSM-5 zeolite (having an Si/Al atomic ratio of 1000), the above-obtained H type ferrierite was mixed with kaolinite "ASP072" (trade name) and the high purity silica sol, to thereby obtain the catalyst (S). The thus obtained catalyst (S) had a composition wherein it comprised 50% by weight of an H type ferrierite, 25% by weight of $SiO_2$ and 25% by weight of kaolinite.

EXAMPLE 1

The catalyst (A) was compression molded and pulverized into particles having a particle size of from 0.5 to 1.5 mm. 1.5 g of the obtained catalyst particles was filled in a quartz glass reactor (having a length of 40 cm and an inner diameter of 12 mm) for use as a fixed-bed reactor, and then the inside of the reactor was maintained at 400° C. for 1 hour under a stream of nitrogen gas at a flow rate of 200 Ncc/min (wherein Ncc means volume (cc) as measured under the normal temperature and pressure conditions, namely, at 0° C. under 1 atm). Then, a reaction was performed under conditions wherein the inside of the reactor was maintained under atmospheric pressure and at 350° C. under a stream of nitrogen gas at a flow rate of 70 Ncc/min, and into the reactor was fed a raw material solution (which was a 35.7% by weight cyclohexanone oxime solution in methanol) at a flow rate of 8.4 g/hour. The weight hourly space velocity in the reactor was 2.0 hour$^{-1}$ (4.0 hour$^{-1}$, as determined, based on the weight of the zeolite component as a most active species). The resultant gaseous reaction mixture was condensed by passing it through a condenser maintained at about 3° C., to thereby obtain a liquid reaction mixture, and the obtained liquid reaction mixture was collected in a trap cooled with ice or a dry ice ethanol. The obtained reaction mixture was analyzed by gas chromatography as described above. The results of the reaction are shown in Table 1.

The conversion of cyclohexanone oxime and the selectivity for ε-caprolactam are calculated as follows:

Conversion (%) of cyclohexanone oxime=$[(O-R)/O] \times 100$

Selectivity (%) for ε-caprolactam=$[L/(O-R)] \times 100$ wherein:
O=mole of cyclohexanone oxime fed (mol/hour)
R=mole of unreacted cyclohexanone oxime (mol/hour)
L=mole of ε-caprolactam produced (mol/hour)

Comparative Example 1

Using the catalyst (B), a reaction was performed under substantially the same conditions as in Example 1. The results are shown in Table 1.

EXAMPLE 2

Using the catalyst (C), a reaction was performed under substantially the same conditions as in Example 1. The results are shown in Table 1. A comparison between the results of this Example 2 and the results of Example 1 shows that, when the catalyst is produced using a high purity silica sol (as in the case of Example 2), the selectivity for the desired product is improved.

Comparative Example 2

Using the catalyst (D), a reaction was performed under substantially the same conditions as in Example 1. The results are shown in Table 1.

EXAMPLE 3

Using the catalyst (E), a reaction was performed under substantially the same conditions as in Example 1. The results are shown in Table 1.

The catalyst (E), containing an alumina as a part of the inorganic oxide, exhibited a selectivity lower than exhibited by the catalyst (C) containing no alumina, but the catalyst (E) exhibited an improved mechanical strength of the catalyst shaped article, as compared to that of the catalyst (C). (For measurement of mechanical strength, each catalyst was individually compression molded under the same pressure, into a cylindrical shape having a diameter of 3 mm and a length of 4 mm. The hardness of each cylindrically shaped catalyst was measured using a Kiya hardness tester.) That is, the catalyst (E) exhibits an advantageous property for commercial use.

Comparative Example 3

Using the catalyst (F), a reaction was performed under substantially the same conditions as in Example 1. The results are shown in Table 1.

EXAMPLE 4

Using the catalyst (G), a reaction was performed under substantially the same conditions as in Example 1. The results are shown in Table 1.

The catalyst (G) exhibited a selectivity lower than exhibited by the catalyst (E), but the catalyst (G) containing a larger amount of alumina, exhibited a further improved mechanical strength of the catalyst shaped article, as compared to that of the catalyst (E). (The hardness of each catalyst was measured in substantially the same manner as in Example 3.) That is, the catalyst (G) exhibits an advantageous property for commercial use.

Comparative Example 4

Using the catalyst (H), a reaction was performed under substantially the same conditions as in Example 1. The results are shown in Table 1.

EXAMPLE 5

Using the catalyst (I), a reaction was performed under substantially the same conditions as in Example 1. The results are shown in Table 1.

EXAMPLE 6

Using the catalyst (J), a reaction was performed under substantially the same conditions as in Example 1. The results are shown in Table 2.

EXAMPLE 7

Using the catalyst (K), a reaction was performed under substantially the same conditions as in Example 1. The results are shown in Table 2.

EXAMPLE 8

Using 1.50 g of the catalyst (L), a reaction was performed under substantially the same conditions as in Example 1, except that a 35.7% by weight cyclohexanone oxime solution in ethylene glycol monomethyl ether (raw material solution) was fed to the reactor at a flow rate of 8.4 g/hour and that the flow rate of nitrogen gas was changed to 106 Ncc/min. The weight hourly space velocity in the reactor was 2.0 hour$^{-1}$ (4.5 hour$^{-1}$, as determined, based on the weight of the zeolite component as a most active species). The results are shown in Table 3.

EXAMPLE 9

Using the catalyst (M), a reaction was performed under substantially the same conditions as in Example 8. The results are shown in Table 3.

EXAMPLE 10

Using the catalyst (N), a reaction was performed under substantially the same conditions as in Example 8. The results are shown in Table 3.

EXAMPLE 11

Using the catalyst (O), a reaction was performed under substantially the same conditions as in Example 8. The results are shown in Table 3.

EXAMPLE 12

Using the catalyst (P), a reaction was performed under substantially the same conditions as in Example 1. The results are shown in Table 4.

EXAMPLE 13

Using the catalyst (Q), a reaction was performed under substantially the same conditions as in Example 1. The results are shown in Table 4.

EXAMPLE 14

Using 1.2 g of the catalyst (R), a reaction was performed under substantially the same conditions as in Example 1, except that a 9.0% by weight cyclohexanone oxime solution in 1-hexanol (raw material solution) was fed to the reactor at a flow rate of 4.4 g/hour and that the flow rate of nitrogen gas was changed to 20 Ncc/min. The weight hourly space velocity in the reactor was 0.33 hour$^{-1}$ (0.66 hour$^{-1}$, as determined, based on the weight of the zeolite component as a most active species). The results are shown in Table 4.

EXAMPLE 15

Using 1.5 g of the catalyst (S), a reaction was performed under substantially the same conditions as in Example 1, except that a 5.0% by weight cyclohexanone oxime solution in 1-hexanol (raw material solution) was fed to the reactor at a flow rate of 5.0 g/hour and that the flow rate of nitrogen gas was changed to 50 Ncc/min. The weight hourly space velocity in the reactor was 0.17 hour$^{-1}$ (0.33 hour$^{-1}$, as determined, based on the weight of the zeolite component as a most active species). The results are shown in Table 4.

EXAMPLE 16

Figure 2:
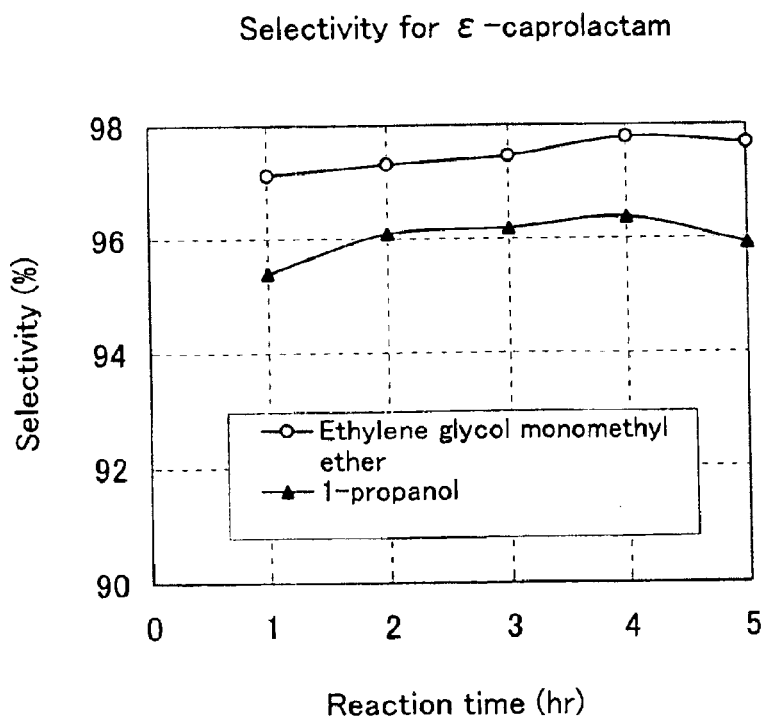
FIG. 2 is a graph showing a comparison in selectivity for ε-caprolactam between Example 16 and Comparative Example 5.

The H type silicalite obtained in Reference Example 1 was compression molded, followed by pulverization. From the resultant particles, particles having a particle size of from 0.5 to 1.5 mm were collected to obtain a catalyst comprised only of a zeolite. Using the thus obtained catalyst, a reaction was performed under substantially the same conditions as in Example 1, except that a 35.7% by weight cyclohexanone oxime solution in ethylene glycol monomethyl ether (raw material solution) was fed to the reactor at a flow rate of 4.2 g/hour and that the flow rate of nitrogen gas was changed to 53 Ncc/min. The weight hourly space velocity in the reactor was 4.0 hour$^{-1}$, as determined, based on the weight of the zeolite component as a most active species. The concentration of cyclohexanone oxime in all gases fed to the reactor was 7.0% by volume. The results are shown in Table 5 and FIGS. 1 and 2.

Comparative Example 5

Using 0.375 g of the same catalyst as used in Example 16, a reaction was-performed under substantially the same conditions as in Example 1, except that a 35.7% by weight cyclohexanone oxime solution in 1-propanol (raw material solution) was fed to the reactor at a flow rate of 4.2 g/hour and that the flow rate of nitrogen gas was changed to 49 Ncc/min. The weight hourly space velocity in the reactor was 4.0 hour$^{-1}$, as determined, based on the weight of the zeolite component as a most active species. The concentration of cyclohexanone oxime in gas all gases fed to the reactor was 7.0% by volume. The results are shown in Table 5 and FIGS. 1 and 2.

The present Comparative Example was performed under the same conditions as in Example 16, so as to compare the method of the present invention (which uses the polyhydric alcohol compound) with a method using a monohydric alcohol having the same number of carbon atoms as in the polyhydric alcohol compound used in Example 16.

EXAMPLE 17

Figure 3:
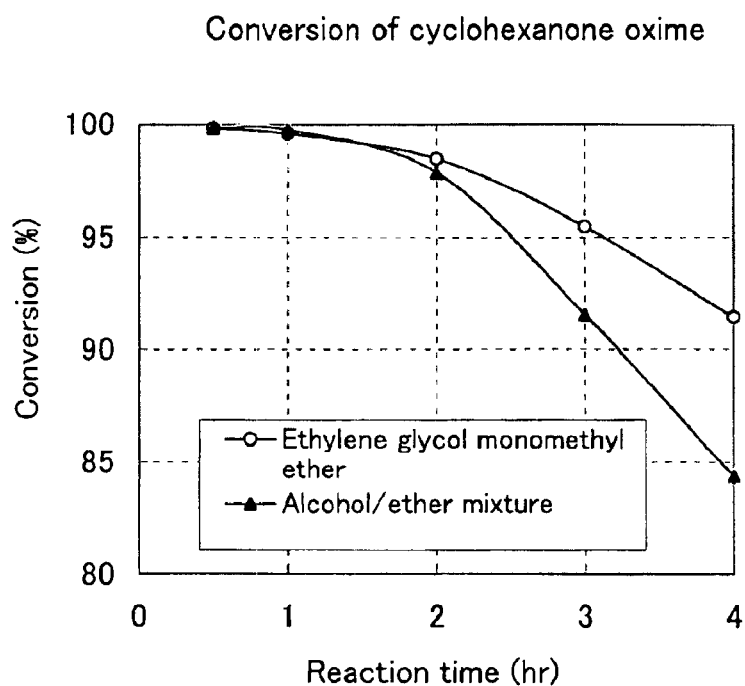
FIG. 3 is a graph showing a comparison in cyclohexanone oxime conversion between Example 17 and Comparative Example 6.
Figure 4:
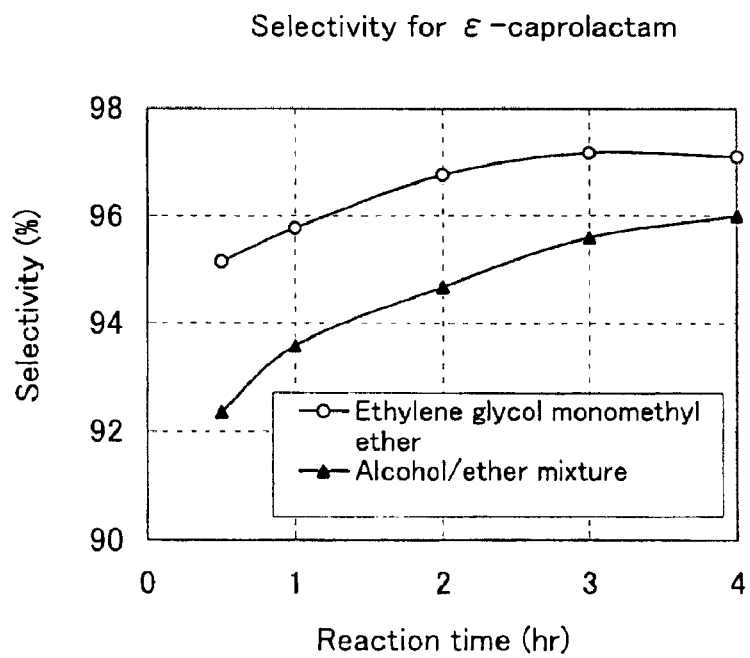
FIG. 4 is a graph showing a comparison in selectivity for ε-caprolactam between Example 17 and Comparative Example 6.

Using 0.375 g of the same catalyst as used in Example 16, a reaction was performed under substantially the same conditions as in Example 1, except that a 45.0% by weight cyclohexanone oxime solution in ethylene glycol monomethyl ether (raw material solution) was fed to the reactor at a flow rate of 3.3 g/hour and that the flow rate of nitrogen gas was changed to 57 Ncc/min. The weight hourly space velocity in the reactor was 4.0 hour$^{-1}$, as determined, based on the weight of the zeolite component as a most active species. The concentration of cyclohexanone oxime in all gases fed to the reactor was 6.9% by volume. The results are shown in Table 5 and FIGS. 3 and 4.

Comparative Example 6

Using 0.375 g of the catalyst same as used in Example 16, a reaction was performed under substantially the same conditions as in Example 1, except that a 45.0% by weight cyclohexanone oxime solution in a mixed solvent of an alcohol (27% by weight of methanol) and an ether (73% by weight of methyl-tert-butyl ether) (alcohol/ether molar ratio=1:1) was fed to the reactor at a flow rate of 3.3 g/hour and that the flow rate of nitrogen gas was changed to 54 Ncc/min. The weight hourly space velocity in the reactor was 4.0 hour$^{-1}$, as determined, based on the weight of the zeolite component as a most active species. The concentration of cyclohexanone oxime in all gases fed to the reactor was 7.2% by volume. The results are shown in Table 5 and FIGS. 3 and 4.

The present Comparative Example was performed under the same conditions as in Example 17, so as to compare the method of the present invention (which uses the polyhydric alcohol compound) with a method using a (1:1 by mole) mixed solvent of a monohydric alcohol and an ether.

EXAMPLE 18

Using 0.375 g of the same catalyst as used in Example 16, a reaction was performed under substantially the same conditions as in Example 1, except that a 20.0% by weight cyclohexanone oxime solution in ethylene glycol monoethyl ether (raw material solution) was fed to the reactor at a flow rate of 7.5 g/hour and that the flow rate of nitrogen gas was changed to 42 Ncc/min. The weight hourly space velocity in the reactor was 4.0 hour$^{-1}$, as determined, based on the weight of the zeolite as a most active species. The concentration of cyclohexanone oxime in all gases fed to the reactor was 6.9% by volume. The results are shown in Table 5.

Comparative Example 7

Using 0.375 g of the same catalyst as used in Example 16, a reaction was performed under substantially the same conditions as in Example 1, except that a 20.0% by weight cyclohexanone oxime solution in 1-hexanol (raw material solution) was fed to the reactor at a flow rate of 7.5 g/hour and that the flow rate of nitrogen gas was changed to 44 Ncc/min. The weight hourly space velocity in the reactor was 4.0 hour$^{-1}$, as determined, based on the weight of the zeolite component as a most active species. The concentration of cyclohexanone oxime in all gases fed to the reactor was 7.0% by volume. The results are shown in Table 5.

EXAMPLE 19

This Example provides an example of the process for preparing the catalyst for use in a fluidized-bed reaction, and an example of the fluidized-bed reaction.

To 2,370 g of sodium silicate (grade: JIS Special-No. 3) (manufactured and sold by Fuji Chemical Co., Ltd., Japan; $SiO_2$ content=25.2% by weight, $Al_2O_3$ content=0.01% by weight, and $SiO_2/Na_2O$ molar ratio=3.3; strongly basic) were added 3,570 g of purified water and 300 g of a sulfuric acid, and the resultant mixture was thoroughly mixed while cooling with ice, and thereto were further added 500 g of kaolinite "ASP072" (trade name) and 900 g of an H type silicalite. The resultant mixture was stirred for 1 hour by using a homogenizer at 5,000 rpm, to thereby obtain a slurry. The obtained slurry was spray dried by using a spray dryer ("Mobile Minor™; manufactured and sold by Niro Japan Co., Ltd., Japan) to thereby obtain a dried catalyst precursor powder. The spray drying was performed by using a two-phase nozzle under conditions wherein the inlet and outlet temperatures of the dryer section of the apparatus were 250° C. and 100° C., respectively, and the slurry feeding rate was 2 kg/hour. Part of the thus obtained dried catalyst precursor powder was dried at 110° C. and then added to 1 M aqueous solution of nitric acid to thereby obtain a slurry having a solids content of 10% by weight. The resultant slurry was maintained at 25° C. for 1 hour, followed by washing with water, drying at 110° C. for 12 hours, and calcination at 600° C. for 5 hours, to thereby obtain powdery catalyst (T). The thus obtained catalyst (T) had a composition wherein it comprised 45% by weight of an H type silicalite, 30% by weight of $SiO_2$, and 25% by weight of kaolinite. The powdery catalyst (T) was composed mainly of spherical particles having a particle diameter within the range of from 50 to 100 μm, as observed under an optical microscope.

The catalyst (T) had an attrition index (I.D.) of 0.2% by weight, as measured by the above-mentioned method. That is, the catalyst used in the present invention exhibits an extremely high attrition resistance, and has practical morphology and mechanical strength which are suitable for use in a fluidized-bed reaction. 40.0 g of the obtained catalyst (T) was filled in a quartz glass reactor (having a length of 60 cm and an inner diameter of 25 mm) for use as a fluidized-bed reactor, and then the catalyst was fluidized at 350° C. for 1 hour under a stream of nitrogen gas at a flow rate of 393 Ncc/min. Then, into the reactor was fed. a 35.7% by weight cyclohexanone oxime solution in ethylene glycol monomethyl ether (raw material solution) at a flow rate of 30.8 g/hour, to thereby perform a reaction under atmospheric pressure. The weight hourly space velocity in the reactor was 0.27 hour$^{-1}$ (0.61 hour$^{-1}$, as determined, based on the weight of the zeolite component as a most active species). The results of the reaction are shown in Table 6.

The results of Example 19 show that when the method of the present invention (in which a solid acid catalyst having a specific composition is used and/or a rearrangement reaction is effected in the presence of a specific polyhydric alcohol compound) is used to perform a fluidized-bed reaction process which is the preferred mode of process in the present invention, the catalyst exhibits excellent performance as in the case where the method of the present invention is used to perform a fixed-bed reaction process (Examples 1 through 18).

TABLE 1

| Catalyst | | First component Zeolite | Second component | | | | Calcination temperature (° C.) | Reaction time (hr) | Conversion of cyclohexanone oxime (%) | Selectivity for ε-caprolactam (%) |
|---|---|---|---|---|---|---|---|---|---|---|
| | | | Crystalline clay mineral | Third component | | | | | | |
| | | Zeolite | | SiO$_2$ | Al$_2$O$_3$ | | | | | |
| Ex. 1 | (A) | H type silicalite | 50 | 25 | 25* | — | 800 | 1 | 99.5 | 90.9 |
| | | | | | | | | 3 | 96.2 | 92.8 |
| Compara. Ex. 1 | (B) | H type silicalite | 50 | — | 50* | — | 800 | 1 | 86.0 | 85.5 |
| | | | | | | | | 3 | 65.0 | 88.5 |
| Ex. 2 | (C) | H type silicalite | 50 | 25 | 25 | — | 800 | 1 | 97.7 | 92.3 |
| | | | | | | | | 3 | 90.9 | 95.0 |
| Compara. Ex. 2 | (D) | H type silicalite | 50 | — | 50 | — | 800 | 1 | 83.9 | 89.2 |
| | | | | | | | | 3 | 56.7 | 91.6 |
| Ex. 3 | (E) | H type silicalite | 50 | 25 | 19 | 6 | 700 | 1 | 99.7 | 81.3 |
| | | | | | | | | 3 | 99.6 | 86.7 |
| Compara. Ex. 3 | (F) | H type silicalite | 50 | — | 38 | 12 | 700 | 1 | 99.3 | 71.8 |
| | | | | | | | | 3 | 99.0 | 76.0 |
| Ex. 4 | (G) | H type silicalite | 50 | 25 | — | 25 | 700 | 1 | 99.9 | 72.9 |
| | | | | | | | | 3 | 83.9 | 82.0 |
| Compara. Ex. 4 | (H) | H type silicalite | 50 | — | — | 50 | 700 | 1 | 99.8 | 61.9 |
| | | | | | | | | 3 | 94.2 | 66.0 |
| Ex. 5 | (I) | H type silicalite | 50 | 10 | 40 | — | 800 | 1 | 98.7 | 94.3 |
| | | | | | | | | 3 | 90.9 | 95.8 |

Notes:
SiO$_2$ marked with the symbol "*" is formed from "SNOWTEX ® STN30" (trade name). Other SiO$_2$ products are formed from a high purity silica sol. As a crystalline clay mineral, kaolinite "ASP072" (trade name) is used.
Feedstock: 35.7% by weight solution of cyclohexanone oxime in methanol. The weight hourly space velocity (W.H.S.V.) of the feedstock in the reactor (as measured based on the zeolite): 4.0 hour$^{-1}$.

TABLE 2

| Catalyst | | Crystalline clay mineral | First component Zeolite | Second component | | | | Calcination temperature (° C.) | Reaction time (hr) | Conversion of cyclohexanone oxime (%) | Selectivity for ε-caprolactam (%) |
|---|---|---|---|---|---|---|---|---|---|---|---|
| | | | | Crystalline clay mineral | Third component | | | | | | |
| | | | Zeolite | | SiO$_2$ | Al$_2$O$_3$ | | | | | |
| Ex. 6 | (J) | Talc | 50 | 25 | 25 | — | 800 | 1 | 96.3 | 95.3 |
| | | | | | | | | 3 | 84.7 | 96.2 |
| Ex. 7 | (K) | Montmorillonite | 50 | 25 | 25 | — | 800 | 1 | 99.8 | 90.0 |
| | | | | | | | | 3 | 90.6 | 93.5 |

Notes:
As the zeolite, an H type silicalite is used.
Feedstock: 35.7% by weight solution of cyclohexanone oxime in methanol. The weight hourly space velocity (W.H.S.V.) of the feedstock in the reactor (as measured based on the zeolite): 4.0 hour$^{-1}$.

TABLE 3

| Catalyst | | Composition of Catalyst (% by weight) | | | | Calcination temperature (° C.) | Reaction time (hr) | Conversion of cyclohexanone oxime (%) | Selectivity for ε-caprolactam (%) |
|---|---|---|---|---|---|---|---|---|---|
| | | Crystalline clay mineral | First component Zeolite | Second component Crystalline clay mineral | Third component | | | | |
| | | | | | SiO$_2$ | Al$_2$O$_3$ | | | | |
| Ex. 8 | (L) | Kaolinite "ASP072" | 45 | 25 | 30** | — | 600 | 1 | 92.0 | 94.7 |
| | | | | | | | | 3 | 79.6 | 96.2 |
| Ex. 9 | (M) | Kaolinite "SP33" | 45 | 25 | 30** | — | 600 | 1 | 87.3 | 94.4 |
| | | | | | | | | 3 | 69.2 | 95.7 |
| Ex. 10 | (N) | Pyrophyllite "5M" | 45 | 15 | 40** | — | 600 | 1 | 88.0 | 94.3 |
| | | | | | | | | 3 | 70.3 | 96.0 |
| Ex. 11 | (O) | Kaolinite "ASP600" | 45 | 25 | 30** | — | 600 | 1 | 93.1 | 94.4 |
| | | | | | | | | 3 | 81.0 | 95.8 |

Notes:
As the zeolite, an H type silicalite is used. The SiO$_2$ marked with the symbol "**" is formed from a sodium silicate (grade: JIS Special No. 3). The SiO$_2$ used as the third component of catalyst (N) is considered to be the amorphous SiO$_2$ contained in the crystalline clay mineral.
Feedscotk: 35.7% by weight solution of cyclohexanone oxime in ethylene glycol monomethyl ether. The weight hourly space velocity (W.H.S.V.) of the feedstock in the reactor (as measured based on the zeolite): 4.5 hour$^{-1}$.

TABLE 4

| Catalyst | | Composition of Catalyst (% by weight) | | | | W.H.S.V. (hr$^{-1}$) | Calcination temperature (° C.) | Reaction time (hr) | Conversion of cyclohexanone oxime (%) | Selectivity for ε-caprolactam (%) |
|---|---|---|---|---|---|---|---|---|---|---|
| | | Zeolite | First component Zeolite | Second component Crystalline clay mineral | Third component SiO$_2$ | | | | | |
| Ex. 12 | (P) | H type titanosilicate | 50 | 25 | 25 | 4.0 | 800 | 1 | 99.5 | 91.0 |
| | | | | | | | | 3 | 95.5 | 94.5 |
| Ex. 13 | (Q) | H type ZSM-5 | 50 | 25 | 25 | 4.0 | 600 | 1 | 99.9 | 94.1 |
| | | | | | | | | 3 | 99.0 | 95.2 |
| Ex. 14 | (R) | H type β type | 50 | 25 | 25 | 0.66 | 600 | 5 | 99.8 | 87.4 |
| Ex. 15 | (S) | H type ferrierite | 50 | 25 | 25 | 0.33 | 600 | 5 | 99.8 | 85.2 |

Notes:
As the crystalline clay mineral, a kaolinite "ASP072" (trade name) is used.
Feedstock: a solution of cyclohexanone oxime in methanol for Examples 12 and 13, a solution of cyclohexanone oxime in 1-hexanol for Examples 14 and 15.
"W.H.S.V." the weight hourly space velocity of the feedstock in the reactor.

TABLE 5

| | Zeolite | Compound copresent in the reactor | Oxime concentration in the gaseous feedstock | W.H.S.V. (hr$^{-1}$) | Reaction time (hr) | Conversion of cyclohexanone oxime (%) | Selectivity for ε-caprolactam (%) |
|---|---|---|---|---|---|---|---|
| Ex. 16 | H type silicalite | Ethylene glycol monomethyl ether | 35.7 | 4.0 | 1 | 98.4 | 97.5 |
| Compara. Ex. 5 | H type silicalite | 1-propanol | 35.7 | 4.0 | 1 | 93.5 | 95.4 |
| Ex. 17 | H type silicalite | Ethylene glycol monomethyl ether | 45.0 | 4.0 | 1 | 99.6 | 95.8 |
| Compara. Ex. 6 | H type silicalite | Mixture (*) | 45.0 | 4.0 | 1 | 99.8 | 93.6 |
| Ex. 18 | H type silicalite | Ethylene glycol monoethyl ether | 20.0 | 4.0 | 1 | 50.0 | 97.0 |

TABLE 5-continued

|  | Zeolite | Compound copresent in the reactor | Oxime concentration in the gaseous feedstock | W.H.S.V. (hr$^{-1}$) | Reaction time (hr) | Conversion of cyclohexanone oxime (%) | Selectivity for ε-caprolactam (%) |
|---|---|---|---|---|---|---|---|
| Compara. Ex. 7 | H type silicalite | 1-hexanol | 20.0 | 4.0 | 1 | 25.4 | 87.3 |

Notes:
The compound marked with the symbol "*" is a mixture of 27% by weight of methanol and 73% by weight of methyl-tert-butyl ether (methanol/methyl-tert-butyl ether molar ratio = 1:1)
W.H.S.V. = the Weight Hourly Space Velocity

TABLE 6

| Catalyst | Zeolite | Composition of Catalyst (% by weight) | | | W.H.S.V. (hr$^{-1}$) | Calcination temperature (° C.) | Reaction time (hr) | Conversion of cyclohexanone oxime (%) | Selectivity for ε-caprolactam (%) |
|---|---|---|---|---|---|---|---|---|---|
| | | First component Zeolite | Second component Crystalline clay mineral | Third component SiO$_2$ | | | | | |
| Ex. 19 (T) | H type silicalite | 45 | 25 | 30** | 0.61 | 600 | 1 | 98.9 | 91.9 |
| | | | | | | | 3 | 98.6 | 94.6 |
| | | | | | | | 5 | 98.9 | 94.8 |
| | | | | | | | 9 | 98.0 | 95.3 |
| | | | | | | | 13 | 97.8 | 95.8 |
| | | | | | | | 17 | 97.5 | 96.6 |
| | | | | | | | 23 | 97.0 | 96.2 |
| | | | | | | | 25 | 96.9 | 96.1 |

Notes:
As the crystalline clay mineral, a kaolinite "ASP072" (product name) is used. The SiO$_2$ marked with the symbol "**" is formed from a sodium silicate (grade: JIS Special No. 3).
Feedstock: 35.7% by weight solution of cyclohexanone oxime in ethylene glycol monomethyl ether. Type of reaction process: fluidized-bed reaction process.
W.H.S.V. = the Weight Hourly Space Velocity

INDUSTRIAL APPLICABILITY

In the production of ε-caprolactam by contacting cyclohexanone oxime with a solid acid catalyst in the gaseous phase to effect a rearrangement reaction of the cyclohexanone oxime, by virtue of using a solid acid catalyst having a specific composition and/or performing the rearrangement reaction in the presence of a specific polyhydric alcohol compound, the desired ε-caprolactam can be produced from cyclohexanone oxime with high selectivity and in high yield.

What is claimed is:

1. A method for producing ε-caprolactam, which comprises contacting cyclohexanone oxime with a solid acid catalyst in a gaseous phase to effect a rearrangement reaction of said cyclohexanone oxime, said solid acid catalyst being produced by calcining a dried catalyst precursor, said catalyst precursor comprising a zeolite, a crystalline clay mineral and at least one substance selected from the group consisting of an inorganic oxide and a compound which forms said inorganic oxide by calcination, wherein said crystalline clay mineral is at least one member selected from the group consisting of a 1:1 clay mineral and a 2:1 clay mineral, said inorganic oxide comprises an oxide of at least one element selected from the group consisting of elements belonging to Groups 4, 13 and 14 of the Periodic Table and wherein said inorganic oxide is other than oxides contained in a crystalline form in said zeolite and said crystalline clay mineral.

2. The method according to claim 1, wherein said zeolite is at least one member selected from the group consisting of an aluminosilicate having an Si/Al atomic ratio of 10 or more, a metallosilicate having an Si/metal atomic ratio of 10 or more and a silicalite.

3. The method according to claim 1 or 2, wherein said zeolite is an MFI zeolite.

4. The method according to claim 1 or 2, wherein said zeolite is at least one member selected from the group consisting of an MFI silicalite and a ZSM-5 zeolite.

5. The method according to claim 1 or 2, wherein said crystalline clay mineral is at least one member selected from the group consisting of a kaolin mineral, a talc, a montmorillonite and a pyrophyllite.

6. The method according to claim 1 or 2, wherein said inorganic oxide is at least one member selected from the group consisting of a silica, a silica-alumina and an alumina.

7. The method according to claim 1 or 2, wherein the amount of said crystalline clay mineral in said dried catalyst precursor is from 5 to 50% by weight, based on the total weight of said zeolite, said crystalline clay mineral and said at least one substance selected from the group consisting of an inorganic oxide and a compound which forms said inorganic oxide by calcination.

8. The method according to claim 1 or 2, wherein said rearrangement reaction of said cyclohexanone oxime is performed under conditions wherein the reaction temperature is from 200 to 500° C., the reaction pressure is from 0.01 to 1 MPa, and a weight hourly space velocity of said cyclohexanone oxime is from 0.01 to 100 hr$^{-1}$.

9. The method according to claim 1 or 2, wherein said rearrangement reaction is performed by a fluidized-bed process.

10. The method according to claim 1 or 2, wherein a part of the catalyst used in said rearrangement reaction is continuously or intermittently withdrawn from a reactor for said rearrangement reaction, whereupon the withdrawn catalyst is regenerated in an atmosphere of oxygen-containing gas or an inert gas, and the regenerated catalyst is recycled to said reactor.

11. A method for producing ε-caprolactam, which comprises contacting cyclohexanone oxime with a solid acid catalyst in a gaseous phase to effect a rearrangement reaction of said cyclohexanone oxime, said rearrangement reaction being effected in the presence of a polyhydric alcohol compound represented by the following formula:

$$R^1\text{—}O\text{—}R^2\text{—}OH$$

wherein:

$R^1$ represents a $C_1$–$C_5$ alkyl group or a phenyl group, and $R^2$ represents a $C_2$–$C_5$ alkylene group, and wherein said solid acid catalyst is a zeolite or a zeolite-containing catalyst.

12. The method according to claim 11, wherein said zeolite is at least one member selected from the group consisting of an aluminosilicate having an Si/Al atomic ratio of 10 or more, a metallosilicate having an Si/metal atomic ratio of 10 or more and a silicalite.

13. The method according to claim 11 or 12, wherein said zeolite is an MFI zeolite.

14. The method according to claim 11 or 12, said polyhydric alcohol compound is at least one member selected from the group consisting of ethylene glycol monomethyl ether, ethylene glycol monoethyl ether, propylene glycol monomethyl ether and propylene glycol monoethyl ether.

15. The method according to claim 11 or 12, wherein said polyhydric alcohol compound is ethylene glycol monomethyl ether.

16. The method according to claim 11 or 12, wherein said rearrangement reaction of said cyclohexanone oxime is performed under conditions wherein the reaction temperature is from 200 to 500° C., the reaction pressure is from 0.01 to 1 MPa, and a weight hourly space velocity of said cyclohexanone oxime is from 0.01 to 100 $hr^{-1}$.

17. The method according to claim 11 or 12, wherein said rearrangement reaction is performed by a fluidized-bed process.

18. The method according to claim 11 or 12, wherein a part of the catalyst used in said rearrangement reaction is continuously or intermittently withdrawn from a reactor for said rearrangement reaction, whereupon the withdrawn catalyst is regenerated in an atmosphere of oxygen-containing gas or an inert gas, and the regenerated catalyst is recycled to said reactor.

* * * * *